United States Patent
Kammer et al.

(10) Patent No.: US 8,852,604 B2
(45) Date of Patent: Oct. 7, 2014

(54) MULTIEPITOPE VACCINE FOR HER2/NEU-ASSOCIATED CANCERS

(75) Inventors: Andreas Kammer, Zollikofen (CH); Mario Amacker, Schmitten (CH); Rinaldo Zurbriggen, Schmitten (CH)

(73) Assignee: Pevion Biotech AG, Ittigen (CH)

( * ) Notice: Subject to any disclaimer, the term of this patent is extended or adjusted under 35 U.S.C. 154(b) by 0 days.

(21) Appl. No.: 13/389,419

(22) PCT Filed: Aug. 18, 2010

(86) PCT No.: PCT/EP2010/005071
§ 371 (c)(1), (2), (4) Date: Apr. 19, 2012

(87) PCT Pub. No.: WO2011/020604
PCT Pub. Date: Feb. 24, 2011

(65) Prior Publication Data
US 2012/0195962 A1   Aug. 2, 2012

(30) Foreign Application Priority Data

Aug. 18, 2009   (EP) .................... 09010627

(51) Int. Cl.
*C07K 19/00* (2006.01)
*C07K 14/71* (2006.01)
*A61K 39/00* (2006.01)

(52) U.S. Cl.
CPC ..... *A61K 39/0011* (2013.01); *A61K 2039/6037* (2013.01); *A61K 2039/55555* (2013.01); *A61K 2039/55577* (2013.01); *C07K 14/71* (2013.01)
USPC ...................................... 424/192.1

(58) Field of Classification Search
None
See application file for complete search history.

(56) References Cited

U.S. PATENT DOCUMENTS

| 7,060,284 | B1 | 6/2006 | Kaumaya et al. | |
| 2006/0275777 | A1 * | 12/2006 | Waelti | 435/6 |

FOREIGN PATENT DOCUMENTS

| CN | 1749276 A | 3/2006 |
| EP | 1236740 A1 | 2/2001 |
| EP | 1844788 A1 | 4/2006 |

OTHER PUBLICATIONS

Dakappagari, et al., "Intracellular delivery of a novel multiepitope peptide vaccine by an amphipathic peptide carrier enhances cytotoxic T-cell responses in HLA-A*201 mice," *J. Peptide Res.*, 2005, 65:189-199.
European Search Report for EP Application No. 09010627.9, filed Aug. 18, 2009.

\* cited by examiner

*Primary Examiner* — Brad Duffy
*Assistant Examiner* — Nelson B Moseley, II
(74) *Attorney, Agent, or Firm* — Saul Ewing, LLP; Kathryn Doyle

(57) ABSTRACT

The present invention includes fusion peptides comprising fragments of the cancer-related protein Her2/neu, methods of preparing such fusion peptides, virosomes comprising such fusion peptides, and uses of such fusion peptides or virosomes for the prevention, treatment or amelioration of a cancer characterized by expression or over-expression of the Her2/neu protein.

15 Claims, 6 Drawing Sheets

MELAALCRWGLLLALLPPGAASTQVCTGTDMKLRLPASPETHLDMLRHLYQGCQVVQGNL
ELTYLPTNASLSFLQDIQEVQGYVLIAHNQVRQVPLQRLRIVRGTQLFEDNYALAVLDNG
DPLNNTTPVTGASPGGLRELQLRSLTEILKGGVLIQRNPQLCYQDTILWKDIFHKNNQLA
LTLIDTNRSRACHPCSPMCKGSRCWGESSEDCQSLTRTVCAGGCARCKGPLPTDCCHEQC
AAGCTGPKHSDCLACLHFNHSGICELHCPALVTYNTDTFESMPNPEGRYTFGASCVTACP
YNYLSTDVGSCTLVCPLHNQEVTAEDGTQRCEKCSKPCARVCYGLGMEHLREVRAVTSAN
IQEFAGCKKIFGSLAFLPESFDGDPASNTAPLQPEQLQVFETLEEITGYLYISAWPDSLP
DLSVFQNLQVIRGRILHNGAYSLTLQGLGISWLGRSLRELGSGLALIHHNTHLCFVHTV
PWDQLFRNPHQALLHTANRPEDECVGEGLACHQLCARGHCWGPGPTQCVNCSQFLRGQEC
VEECRVLQGLPREYVNARHCLPCHPECQPQNGSVTCFGPEADQCVACAHYKDPPFCVARC
PSGVKPDLSYMPIWKFPDEEGACQPCPINCTHSCVDLDDKGCPAEQRASPLTSIISAVVG
ILLVVVLGVVFGILIKRRQQKIRKYTMRRLLQETELVEPLTPSGAMPNQAQMRILKETEL
RKVKVLGSGAFGTVYKGIWIPDGENVKIPVAIKVLRENTSPKANKEILDEAYVMAGVGSP
YVSRLLGICLTSTVQLVTQLMPYGCLLDHVRENRGRLGSQDLLNWCMQIAKGMSYLEDVR
LVHRDLAARNVLVKSPNHVKITDFGLARLLDIDETEYHADGGKVPIKWMALESILRRRFT
HQSDVWSYGVTVWELMTFGAKPYDGIPAREIPDLLEKGERLPQPPICTIDVYMIMVKCWM
IDSECRPRFRELVSEFSRMARDPQRFVVIQNEDLGPASPLDSTFYRSLLEDDDMGDLVDA
EEYLVPQQGFFCPDPAPGAGGMVHHRHRSSSTRSGGGDLTLGLEPSEEEAPRSPLAPSEG
AGSDVFDGDLGMGAAKGLQSLPTHDPSPLQRYSEDPTVPLPSETDGYVAPLTCSPQPEYV
NQPDVRPQPPSPREGPLPAARPAGATLERPKTLSPGKNGVVKDVFAFGGAVENPEYLTPQ
GGAAPQPHPPPAFSPAFDNLYYWDQDPPERGAPPSTFKGTPTAENPEYLGLDVPV

MULTIEPITOPE VACCINE FOR HER2/NEU-ASSOCIATED CANCERS

FIELD OF THE INVENTION

The present invention relates to fusion peptides comprising fragments of the cancer-related protein Her2/neu, methods of preparing such fusion peptides, virosomes comprising such fusion peptides, and uses of such fusion peptides and/or virosomes for the prevention, treatment and/or amelioration of a cancer characterized by expression or over-expression of the Her2/neu protein,

BACKGROUND OF THE INVENTION

The Her2/neu tumor antigen, encoded by the erbB2/neu protooncogene, is a 185 kDa protein that belongs to the human epidermal growth factor receptor family. It consists of a cysteine-rich extracellular domain (ECD, from amino acids 23 to 652) with several glycosylation sites, a hydrophobic transmembrane domain (from amino acids 653 to 675) and an intracellular tyrosine kinase domain (from amino acids 676 to 1255). The Her2/neu receptor is expressed on the cell membrane of a variety of epithelial cell types and regulates aspects of cell growth and division through binding of specific growth factors. Her2/neu is expressed at low levels in many normal cells, but is over-expressed in a variety of cancers, including breast, ovarian, endometrial, gastric, pancreatic, prostate and salivary gland cancers.

For example, approximately 30% of metastatic breast cancers have been shown to over-express Her2/neu. This over expression is associated with a poor prognosis for the breast cancer patient, as it corresponds to decreased relapse-free periods and shortened survival time. Currently the most common forms of treating breast cancer involve surgery, chemical intervention and/or radiotherapy. Unless the cancer is restricted to a defined area, surgery alone cannot eliminate the cancer. Radiation treatment as well as chemotherapy may entail severe negative side effects.

In view of the disadvantages of the present therapies, attempts have been made to find additional approaches for treating e.g. breast cancer. One such approach is immunotherapy. One of the targets for an immunotherapeutic approach is the Her2/neu protein.

The clinical implications of Her2/neu over-expression in tumors have made Her2/neu an attractive target for antibody-mediated immunotherapy as an adjunct to conventional chemotherapy. However, the monoclonal antibody Trastuzumab (marketed as Herceptin®) is only effective in breast cancer where the Her2/neu receptor is over-expressed. Furthermore multiple infusions are required, resulting in high treatment costs.

Besides immunotherapy via passive immunization with monoclonal antibodies, further efforts have been focused on the active immunization and the identification of antigens recognized by human B- and T-lymphocytes. Such vaccine immunotherapy for cancer has been based on antigens against which humoral and/or cellular responses are elicited. These antigens should ideally be expressed or over expressed exclusively by the tumor and have been termed tumor-associated antigens (TAAs). One of the first TAAs described for breast cancer was HER2/neu. Meanwhile various TAAs representing different epitopes have been tested but so far none successfully passed product development.

In vaccinology, antigens intended to elicit an immune response are sometimes combined with one or more adjuvants, e.g. conjugated or otherwise associated with one or more delivery systems. Depending on the type of immune response intended (B or T cell response), different strategies are applied.

To induce a B cell (i.e. antibody) response the antigens should be B cell epitopes. As generally understood in the art, a B cell epitope is a part of an antigen that is recognized and bound by a B cell receptor. Lipids, polysaccharides and proteins/peptides may contain B cell epitopes which, upon introduction into an organism of choice, cause B cells to produce antibodies which specifically bind to the introduced epitope. The immunogenicity of some B cell epitopes can in some cases be increased by coupling to a suitable delivery system. Coupling of antigens intended to function as B cell epitopes to particles in a repetitive arrangement presumably enables cross-linking of the immunoglobulin receptors on the B cells, which is known to be an exceptionally strong activation signal. Repetitive arrangement can occur via fusion of the B cell epitope with a delivery system including e.g. hepatitis B core (HBc), keyhole limpet hemocyanins (KLH), tetanus toxoid (TT) and/or virosomes. For some B cell antigens T cell help can also enhance antibody production.

A promising approach of antitumor activity is based on the induction of tumor specific humoral immune responses; numerous antibodies directed against the extracellular domain (ECD) of Her2/neu have been generated by immunizing mice with cells expressing Her2/neu. The biological effect of these antibodies appears epitope-specific, that is it is based on specific recognition of a short subsequence within the Her2/neu ECD. Some antibodies have no effect or even actively stimulate tumor growth. The monoclonal antibody (mAb) 4D5 has been shown to reduce the growth of Her2/neu expressing tumors in mice by direct and indirect mechanisms such as apoptosis, antibody-dependent cell-mediated cytotoxicity (ADCC) or complement-dependent cytotoxicity (CDC). Based on these results, a humanized form of this antibody, termed Trastuzumab (Herceptin®), was tested in clinical trials. Increased overall survival of patients with breast tumors overexpressing Her2/neu was observed following cytotoxic treatment plus Herceptin® as compared to chemotherapy or Trastuzumab alone. Herceptin® is now used as monotherapy but shows even higher efficacy in combination with cytotoxic chemotherapy.

Individual fragments of the ECD of Her2/neu are known in the art. For example, WO 2002/068474 (EP 1236740) relates to a vaccine that comprises a peptide of 9-25 amino acids which sequence occurs in the extracellular part of the Her2/neu protein. Further, WO 2007/118660 (EP 1884788) describes a multi-peptide vaccine comprising a specific combination of peptides presenting different amino acid sequences as occur in the extracellular part of the Her2/neu protein. These peptides in these publications may be administered individually or together, in the form of multiple discrete peptides, each preferably conjugated separately to a delivery system.

It is an aim of the present invention to provide improved substances suitable for use as the active components of a vaccine, as well as the corresponding vaccines themselves, for treating, preventing and/or ameliorating Her2-associated cancer. Ideally, such substances should improve upon the protective effect conferred by existing immunotherapies for such cancers while avoiding the need for laborious preparation techniques.

SUMMARY OF THE INVENTION

Accordingly, one aspect of the invention provides a fusion peptide comprising three non-contiguous B cell epitopes from the extracellular domain (ECD) of Her2/neu, or derivatives thereof, linked to one another in a single polypeptide chain.

In a further aspect, the present invention provides a method of preparing a fusion peptide as above. The fusion peptide may be prepared by a peptide synthesis method comprising (i) sequential formation of peptide bonds linking each amino acid to its respectively neighboring amino acid and (ii) recovering said fusion peptide. Alternatively, the fusion peptide may be prepared by a recombinant method comprising (i) providing a nucleic acid comprising a nucleic acid sequence encoding a fusion peptide comprising three non-contiguous B cell epitopes from the extracellular domain (ECD) of Her2/neu, or derivatives thereof, linked to one another in a single polypeptide chain, (ii) transfecting said nucleic acid into a host cell capable of expressing said nucleic acid sequence; (iii) incubating said host cell under conditions suitable for the expression of said nucleic acid sequence; and (iv) recovering said fusion peptide.

In a further aspect, the present invention provides a delivery system covalently and/or non-covalently associated with a fusion peptide as described above or with a fusion peptide obtainable by the above method.

In a further aspect, the present invention provides a fusion peptide as described above and/or a fusion peptide obtainable by the above method and/or a delivery system as described above for use as a medicament.

In a further aspect, the present invention provides a composition comprising a fusion peptide as described above and/or a fusion peptide obtainable by a method as described above and/or a delivery system as described above. In a related aspect, the composition additionally comprises a pharmaceutically acceptable carrier and is a pharmaceutical composition. The composition, e.g. comprising a fusion peptide as described above, may additionally comprise an immunopotentiator.

In a further aspect, the present invention provides a use of a fusion peptide as described above, a fusion peptide obtainable according to a method as described above, a delivery system as described above, a composition as described above and/or a pharmaceutical composition as described above for the preparation of a medicament for the prevention, treatment and/or amelioration of a cancer characterized by expression or over-expression of Her2/neu.

In a further aspect, the present invention provides a method of preventing, treating and/or ameliorating a cancer characterized by expression or over-expression of Her2 in a patient in need or suspected need thereof, comprising the step of administering to said patient an effective amount of a fusion peptide as described above, a fusion peptide obtainable according to a method as described above, a delivery system as described above, a composition as described above and/or a pharmaceutical composition as described above.

BRIEF DESCRIPTION OF THE FIGURES

FIG. 6 Native sequence of human Her2/neu as accessible from the SwissProt database under accession number P04626 (ERBB2_HUMAN), designated herein as SEQ ID NO: 11.

Figure 1:
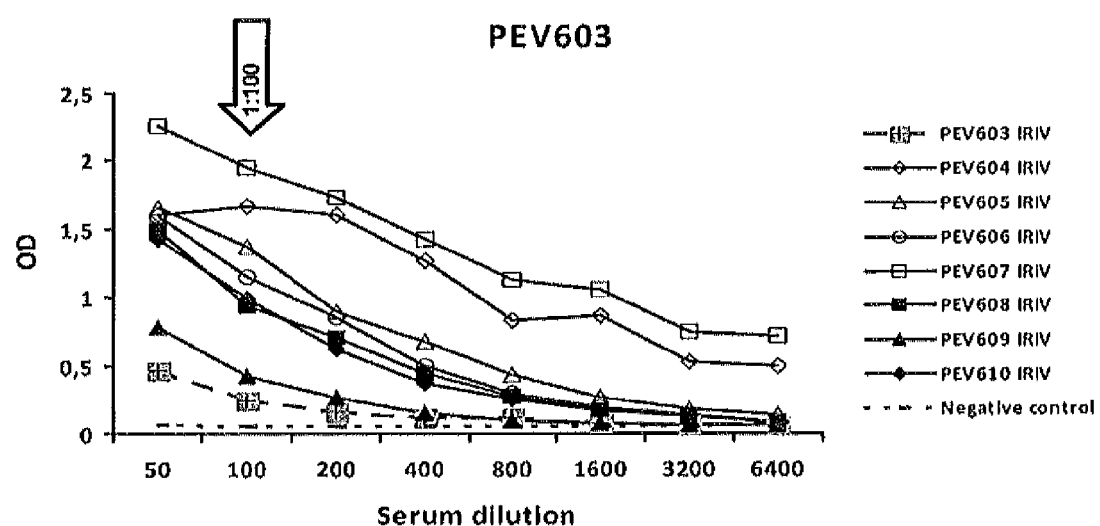
FIG. 1 Representative demonstration that fusion peptides according to the invention induce higher antibody levels against a given B cell epitope than induced by a single peptide containing only that B cell epitope. The antibody levels were measured by ELISA performed on pooled serum obtained from individual mice immunized with the substances indicated in the figure. ELISA plates were coated with PEV603 (SEQ ID NO: 3). The presence of antibody specifically binding to PEV603 in serum is expressed as absorbance (OD) at 492 nm. Absorbance curves obtained using sera from mice immunized with virosomes comprising fusion peptides according to the invention (comprising multiple B cell epitopes) are solid, while that obtained using serum from a mouse immunized with the single-epitope peptide fragment PEV603 is dashed. As can be seen in the figure, the antibody response against PEV603 is higher when PEV603 is incorporated as one of several B cell epitopes in a fusion peptide on a single polypeptide chain. This indicates that fusion of a single given fragment, i.e. a single given B cell epitope, to other B cell epitopes within a single polypeptide chain can elicit a more potent antibody response against this given epitope than elicited by that epitope alone.

Amino acids 23-652 correspond to the ECD of Her2/neu, and are underlined for emphasis in FIG. 6.

DETAILED DESCRIPTION OF THE INVENTION

As described above, one aspect of the invention provides a fusion peptide comprising three non-contiguous B cell epitopes from the extracellular domain (ECD) of Her2/neu, or derivatives thereof, linked to one another in a single polypeptide chain.

It has surprisingly been found that a fusion peptide comprising multiple fragments, i.e. multiple B cell epitopes, from the ECD of Her2/neu can elicit a specific protective immune response which is superior to that elicited by the respective separate single-epitope peptide fragments comprised therein. Further, and significantly, the magnitude of the immune response elicited by a fusion peptide comprising at least three natively non-contiguous B cell epitopes from the EGO of Her2/neu, or derivatives thereof, is greater that what would be expected as the additive sum elicited by its constituent parts in isolation. That is, linking at least three natively non-contiguous B cell epitopes from the ECD of Her2/neu, or derivatives thereof, into a single polypeptide chain results in an advantageous synergism, allowing one to achieve a host immunogenic response against the ECD of endogenous Her2/neu which is stronger than that achievable by administering the corresponding epitopes as single peptide fragment(s).

Seen from the standpoint of a given single B cell epitope within the ECD of Her2/neu (say, epitope A in fragment A), this means that a more potent immune response against epitope A may be achieved when fragment A is linked to another natively non-contiguous epitope from the ECD of Her2/neu (say, fragment B containing epitope B) in a single polypeptide chain, than if fragments A and B were administered alone or together as two discrete peptides. The induction of a strong antibody response in a vaccinated animal can be potentiated further by covalently and/or non-covalently associating the inventive fusion peptide with a delivery system, e.g. for enhanced stimulation of antigen-specific B cells.

Seen from the standpoint of the sum of total antibody responses attributable to all B cell epitopes within a fusion peptide—said sum being representative of the strength of total immunogenicity against native Her2/neu elicited by the inventive fusion peptide—this sum exceeds what would be expected as the additive result of the individual immunogenicities observed for the individual constituent peptide fragments.

Thus, the total immunogenicity elicited by the inventive fusion peptide surprisingly and advantageously exceeds the sum of its parts, so linking B cell epitopes from the ECO of Her2/neu in a fusion peptide according to the invention advantageously allows one to tap immunogenic potential in these fragments which would otherwise remain unharnessed. This increases the host immune stimulation and therefore efficacy of a vaccination regimen employing such fusion peptides in the prevention, treatment and/or amelioration of cancer characterized by expression or over-expression of Her2/neu, for example breast cancer.

However, the inventive fusion peptide allows other advantages as well. Up until now, design of immunoprevention and/or immunotherapy for Her2/neu-expressing or Her2/neu-over-expressing cancer based on multiple epitopes/peptides has entailed administration of such peptides as discrete substances. This has implied certain disadvantages. For example, simultaneous administration of multiple peptides within the same solution runs the risk that these peptides will aggregate with one another, thereby decreasing their intended availability to the host immune system. In extreme cases, the solubility of such aggregates may decrease such that the aggregates precipitate, becoming unavailable to the host immune system. At the same time, separate administration of such peptides in different solutions and at different time points decreases the likelihood that the immunogenic effects of such peptides may combine in an advantageous manner.

Further difficulties with existing multiple single epitopes/peptides can arise when these are used with certain types of delivery systems such as for example virosomes, liposomes or virus-like particles (VLPs). To allow reproducible vaccine production it is necessary to present the antigens in defined concentrations. However, when coupling (i.e. covalently associating) multiple peptide fragments to a single delivery system, such as a single virosome or liposome; it is difficult to ensure that the same number of peptide fragments/epitopes is bound to each delivery system. Fluctuations in coupling number per delivery system invariably exist; while one can be fairly certain that each viable delivery system will be coupled to, say, each of epitopes A and B, some delivery systems will be associated with slightly more of epitope A than intended, while epitope B will slightly exceed intended amounts in others. White the Gaussian distribution of epitopes A and B will tend to center on the intended ratio of fragments A:B, any Gaussian distribution by definition contains outliers, and it is these outliers which potentially detract from maximal immunogenic efficacy, and which become increasingly costly and laborious to exclude as the requirements for maintaining the intended epitope ratio in the delivery system become more stringent. Similar concerns apply when combining delivery systems, e.g. virosomes, associated with different epitope fragments in an attempt to realize a desired ratio of one Her2/neu ECD fragment to another.

The inventive fusion peptide elegantly overcomes the above disadvantages.

By linking at least three non-contiguous B cell epitopes from the ECD of Her2/neu, or derivatives thereof. In a single polypeptide chain, a completely homogeneous formulation can be achieved in which only one kind of polypeptide chain is present. The elements of this polypeptide, i.e. the epitopes of the ECD of Her2/neu which in the native ECD are non-contiguous, are the same in every peptide, and can be chosen (or chosen and modified) such that undesired intra-as well as inter-polypeptide interactions are minimized.

Further, since a corresponding vaccine will contain only a single type of polypeptide, namely the inventive fusion peptide, the ratio of peptidic epitopes present is ultimately dictated by the ratio of these fragments in any given polypeptide molecule. This means that any desired ratio for eliciting an immunogenic response can be easily and reliably fixed at the level of fusion peptide construction and design.

Finally, when using certain delivery systems, for example virosomes, liposomes or VLPs, to deliver the inventive fusion peptide, concerns relating to relative distribution of multiple Her2/neu epitopes, either within a given member of the delivery system population or over the whole delivery system population, effectively disappear. In any given member, only one type polypeptide will be present: the fusion peptide itself. This means that the ratio of one Her2/neu epitope to any other natively non-contiguous epitope thereof will remain constant regardless of how many fusion peptides are associated with a given member of the delivery system population since, as mentioned above, this ratio is determined at the level of a single fusion peptide. While delivery systems associated with more fusion peptides will likely be more immunogenic than delivery systems associated with fewer fusion peptides, the immunogenicity attributable to any given epitope of the Her2/neu ECD remains advantageously and predictably constant.

In summary, the inventive fusion peptide synergistically potentiates the immune response obtainable from Her2/neu epitopes by rendering them easily accessible to the epitope-specific host B cell. This elicits an efficient and predictable antibody immune response against the corresponding desired antigen which is more potent than that obtainable using separate epitopes individually, while avoiding the drawbacks of (a) complex manufacturing processes involving mixing of several intermediate products to obtain the final vaccine and (b) possible chemical interactions between different single epitope fragments which could degrade the efficacy of the resulting vaccine formulation. Finally, the construction of the inventive fusion peptide implies that the number of epitopes available for immune stimulation is maximized, while simultaneously minimizing the number of linkage sites required to ensure immune stimulation.

As used herein, the terms "peptide" and "polypeptide" are used in their broadest sense to refer to a molecule of two or more amino acid residues, or amino acid analogs. The amino acid residues may be linked by peptide bonds, or alternatively by other bonds, e.g. ester, ether etc., but in most cases will be linked by peptide bonds.

As used herein, the terms "amino acid" or "amino acid residue" encompass both natural and unnatural or synthetic amino acids, including both the D- or L-forms, and amino acid analogs. An "amino acid analog" is to be understood as a non-naturally occurring amino acid differing from its corresponding naturally occurring amino acid at one or more atoms. For example, an amino acid analog of cysteine may be homocysteine.

As used herein, the term "fusion peptide" refers to a non-native peptide composed of multiple individual peptide units, in this case non-contiguous B cell epitopes of the ECO of Her2/neu, linked to one another e.g. via peptide (amide) bonds. The fusion peptide comprises at least three B cell epitopes of the ECD of Her2/neu linked in this way, said epitopes being non-contiguous in their native state, i.e. in the ECD of Her2/neu.

As used herein, the term "B cell epitope" refers to a part of a molecule that is recognized by a B cell receptor (antibody). In the context of the present invention, the "B cell epitope" is one of the at least three individual natively non-contiguous epitopic fragments of the ECD of Her2/neu which are comprised in the fusion peptide. In its broadest sense as used herein, a "B cell epitope" is to be understood as a small subsequence of an antigen, said epitope subsequence being recognized by an antibody. An antigen may contain multiple B cell epitopes, and therefore may be bound by multiple distinct antibodies, but any given epitopic fragment of this antigen will be bound by only a specific antibody. Accordingly, the peptide fragments comprised in the inventive fusion peptide should be understood as each containing a single B cell epitope. Thus, by dint of containing multiple B cell epitopes of the ECD of Her2/neu, the inventive fusion peptide may be regarded as a multi-epitope fusion peptide, and a composition, e.g. a vaccine composition comprising the fusion peptide of the invention may be regarded as a multi-epitope composition or a multi-epitope vaccine composition.

It is generally known how to determine whether or not a peptide in question is a "B cell epitope" in the sense of the invention. For example, a peptide in question may be identified with a high degree of accuracy as being or comprising a "B cell epitope" using established computer programs which compare the sequence of the peptide in question with a database of known sequences and/or partial sequences known to be recognized by antibodies encoded by the human or mouse germline. Alternatively, a "B cell epitope" within a given protein may be identified by computer-aided analysis using various combinations of correlates of antigenicity like surface accessibility, chain flexibility, hydropathy/hydrophilicity profiles, predicted secondary structure, etc. Alternatively, a peptide in question may be identified as being or comprising a "B cell epitope" by immunizing an animal with the peptide in question at least once, allowing an immune response to mount and then testing the serum of the animal for antibodies specifically binding to at least a part of the peptide in question. A more detailed description of how to determine whether or not a peptide in question is a "B cell epitope" in the sense of the present invention is provided below in Example 14.

Table 1 sets out the sequences which are "B cell epitopes" of the extracellular domain of the Her2/neu protein in the sense of the invention.

TABLE 1

| B cell epitope | SEQ ID NO |
|---|---|
| PESFDGDPASNTAPLQPGGGGGC | 1 |
| RVLQGLPREYVNARHC | 2 |
| YMPIWKFPDEEGAC | 3 |
| PESFDGDPASNTAPLQP | 12 |
| CAHYKDPPFCVARCPS | 13 |
| YGLGMEHLREVRAVTS | 14 |
| LGSGLALIHHNTHLCF | 15 |
| EVTAEDGTQRCEKCSK | 16 |
| GASCVTACPYNYLSTD | 17 |
| AAGCTGPKHSDCLACL | 18 |
| LEEITGYLYISAWPDS | 19 |
| TQRCEKCSKPCARVCY | 20 |
| GHCWGPGPTQCVNCSQ | 21 |
| MPIWKFPDEEGACQPC | 22 |
| PASNTAPLQPEQLQVF | 23 |
| PEGRYTFGASCVTACP | 24 |
| ASTQVCTGTDMKLRLP | 25 |
| ACHPCSPMCKGSRCWG | 26 |
| QDTILWKDIFHKNNQL | 27 |
| GPEADQCVACAHYKDP | 28 |
| SRCWGESSEDCQSLTR | 29 |
| PASPETHLDMLRHLYQ | 30 |
| YVNARHCLPCHPECQP | 31 |
| HSDCLACLHFNHSGIC | 32 |
| ALTLIDTNRSRACHPC | 33 |
| ALAVLDNGDPLNNTTP | 34 |
| ALVTYNTDTFESMPNP | 35 |

TABLE 1-continued

| B cell epitope | SEQ ID NO |
|---|---|
| RCKGPLPTDCCHEQCA | 36 |
| QPCPINCTHSCVDLDD | 37 |
| VARCPSGVKPDLSYMP | 38 |
| VHTVPWDQLFRNPHQA | 39 |
| YISAWPDSLPDLSVFQ | 40 |
| CKKIFGSLAFLPESFD | 41 |
| NGDPLNNTTPVTGASP | 42 |
| LQDIQEVQGYVLIAHN | 43 |
| VCAGGCARCKGPLPTD | 44 |
| HPECQPQNGSVTCFGP | 45 |
| GVLIQRNPQLCYQDTI | 46 |
| LQVIRGRILHNGAYSL | 47 |
| ESFDGDPASNTAPLQP | 48 |
| ACPYNYLSTDVGSCTL | 49 |
| PVTGASPGGLRELQLR | 50 |
| CVDLDDKGCPAEQRAS | 51 |
| NHSGICELHCPALVTY | 52 |
| GSVTCFGPEADQCVAC | 53 |
| WGLLLALLPPGAASTQ | 54 |
| FLRGQECVEECRVLQG | 55 |
| GTQLFEDNYALAVLDN | 56 |
| GVKPDLSYMPIWKFPD | 57 |

As used herein, the term "derivative" refers to the result of substituting at least one amino acid in a native (i.e. naturally occurring) B cell epitope of the Her2/neu ECD with another amino acid not present at that position of Her2/neu such that the amino acid substitution remains conservative. Derivatives may be made in order to increase the stability of the fusion peptide in the intermediate and end products or to increase the solubility of the fusion peptide in the intermediate and end products or to increase the immunogenicity of fusion peptides. Any method for preparing derivatives can be employed, such as synthesis of derivatives or its recombinant production using a mutated nucleic acid molecule. Further, a "derivative" in the sense of the present invention will retain its quality as a "B cell epitope", measured as described herein. With regard to this characteristic, then, a "derivative" denotes a "functional derivative" in which the substitution does not, or does not completely abolish the capacity of the parent "B cell epitope" to remain a "B cell epitope".

The identification of additional or optimized immunostimulatory fusion peptides may also include the step of comparing the stimulation of B cells by the fusion peptide and the stimulation of B cells by the derivative as a determination of the effectiveness of the stimulation of immune effector cells by the derivative. By comparing the derivative with a known fusion peptide, peptides with increased immune cell stimulatory properties can be prepared.

As used herein, a "conservative substitution" refers to changing amino acid identity at a given position to replace with an amino acid of approximately equivalent size, charge and/or polarity. Examples of natural conservative substitutions of amino acids include the following 8 substitution groups (designated by the conventional one-letter code): (1) M, I, L, V; (2) F, Y, W; (3) K, R, (4) A, G; (5) S, T; (6) Q, N; (7) E, D; and (8) C, S.

A "derivative" as used herein may also result from amino acid substitutions which are functionally equivalent. As used herein, these are to be understood as amino acid substitutions which, when effected, result in a fusion peptide which will give an identical or comparable (i.e. within 10%) ELISA reading based on serum from an animal to which the fusion peptide comprising a derivatized epitopic fragment or derivatized epitopic fragments has/have been administered, as compared to a fusion peptide without corresponding derivatizations. The antigenicity of a fusion peptide according to the invention may for example be determined by measuring the titer of antibodies elicited by immunization of animals by ELISA, such as described in Example 4.2. An analogous process can be used to assay for the functional equivalence of an amino acid substitution, conservative or otherwise. Here, the immune response elicited by a fusion peptide comprising a non-derivatized, "parental" fragment is compared—using the same assay—to that elicited by a fusion peptide comprising the derivatized fragment. If the immune response elicited by the fusion peptide comprising the derivatized fragment is as strong as that elicited by the fusion peptide with the non-derivatized fragment, then the amino acid substitution is to be regarded as functionally equivalent. If the derivatized immune response is superior to the non-derivatized one, then the amino acid substitution is to be regarded as improved.

As used herein, the term "link" and "linked" includes direct linkage of two non-contiguous Her2/neu B cell epitopes via a peptide bond (i.e. the C-terminus of one Her2/neu epitope is covalently bound via a peptide bond to the N-terminal of another, natively non-contiguous epitope). Also included in the meaning of this term, as discussed further below, is the linkage of two natively non-contiguous Her2/neu epitopes via an interposed linker element.

In one embodiment of the fusion peptide, at least two of said B cell epitopes or derivatives thereof are linked to one another via a non-native linker peptide sequence.

As used herein, the term "linker" refers to a short polypeptide sequence interposed between any two neighboring Her2/neu epitopes or derivatives thereof within the fusion peptide. If a linker is included, it is preferably a polypeptide linker of 1-10, preferably 1, 2, 3, 4 or 5 amino acids (inclusive) of any sort (i.e. naturally or non-naturally occurring). The linker may also be a carbohydrate linker, e.g. 5-aminopentanoic acid. It is also possible to include one or more peptidic or polypeptidic linker(s) in the same fusion peptide together with one or more other non-peptidic or non-polypeptidic linker(s). Further, different types of linkers, peptidic or non-peptidic, may be incorporated in the same fusion peptide as deemed appropriate. In the event that a peptidic or polypeptidic linker is used to join two respective epitopic fragments from the ECD of Her2/neu, the linker will be advantageously incorporated such that its N-terminal end is bound via a peptide bond to the C-terminal end of the one fragment, and its C-terminal end via a peptide bond to the N-terminal end of the other fragment. The individual B cell epitopic fragments within the fusion peptide may also have one or more amino acids added to either or both ends, preferably to the C-terminal end. Thus, for example, linker or spacer amino acids may be added to the N- or C-terminus of the peptides or both, to link the non-contiguous peptides and to allow for convenient coupling of the peptides to each other and/or to a delivery system such as a virosome via a lipid molecule in the virosome serving as an anchor. Especially if used for coupling a fusion peptide to a delivery system such as a virosome via a linker, it is preferable to effect such linker-mediated coupling from the C-terminus of the fusion peptide, since linker coupling from the N-terminus has in some instances been observed to negatively influence the desired immune response to be elicited.

As used herein, the terms "native" and "natural" refer to the form of a molecule as normally occurring in nature. As such, the "native" sequence of the ECD of Her2/neu refers to the sequence of Her2/neu from amino acids 23-652 inclusive (underlined portion of FIG. 6). The sequence of native Her2/neu is known and is publicly available in the Swiss-Prot database under accession number P04626 (ERBB2_HUMAN) (http://www.uniprot.org/uniprot/P04626). Conversely, a "non-native" sequence, including a "non-native linker" is any amino acid sequence not belonging to ECD of Her2/neu as set out in FIG. 6. Accordingly, a peptidic "non-native linker" does not represent an extension of either of the Her2/neu fragments which to which it connects into the adjoining native sequence of Her2/neu.

According to a further embodiment the three non-contiguous fragments from the ECD of Her2/neu comprised in the fusion peptide of the invention are selected from the list consisting of: PEV601 (SEQ ID NO: 1), PEV602 (SEQ ID NO: 2), PEV603 (SEQ ID NO: 3), PEV611 (SEQ ID NO: 12), SEQ ID NOs: 13-57 and derivatives thereof. None of these peptides are contiguous in native Her2/neu. As demonstrated in the appended examples, linking any one of these three fragments with any other two in a single polypeptide chain results in a more potent immunogenic response when the resulting fusion peptide is administered to a host, than when the corresponding fragment is administered either alone as a discrete fragment, either alone or together with one or more other discrete epitopic fragment(s).

For example, such a fusion peptide may comprise or consist of three of the amino acid sequences chosen from the list consisting of: PEV601 or PEV611 (SEQ ID NO: 1 or SEQ ID NO: 12, respectively), PEV602 (SEQ ID NO: 2), PEV603 (SEQ ID NO: 3), and SEQ ID NOs: 13-57 and/or derivatives thereof. Combinations of PEV611 (SEQ ID NO: 12), PEV2 (SEQ ID NO: 2) and PEV3 (SEQ ID NO: 3) are preferred. Accordingly, such a fusion peptide may for example comprise or consist of an amino acid sequence of PEV604 (SEQ ID NO: 4), PEV605 (SEQ ID NO: 5), PEV606 (SEQ ID NO: 6), PEV607 (SEQ ID NO: 7), PEV608 (SEQ ID NO: 8), PEV609 (SEQ ID NO: 9) and/or PEV610 (SEQ ID NO: 10). Alternatively, these amino acid sequences may also be concatenated two or more times in tandem repeat within the same fusion peptide and/or combined with one another within the same fusion peptide. Fusion peptides comprising or consisting of an amino acid sequence of PEV604 (SEQ ID NO: 4), PEV605 (SEQ ID NO: 5), PEV606 (SEQ ID NO: 6), PEV607 (SEQ ID NO: 7), PEV608 (SEQ ID NO: 8) and/or PEV610 (SEQ ID NO: 10) are preferred, with fusion peptides comprising or consisting of an amino add sequence of PEV604 (SEQ ID NO: 4), PEV605 (SEQ ID NO: 5), PEV606 (SEQ ID NO: 6), PEV607 (SEQ ID NO: 7) and/or PEV608 (SEQ ID NO: 8) being more preferred. Most preferred, the fusion peptide comprises or consists of an amino acids sequence of PEV604 (SEQ ID NO: 4), PEV606 (SEQ ID NO: 6) and/or PEV607 (SEQ ID NO: 7).

The following table (Table 2) summarizes selected B cell epitopes as well as various preferred embodiments of the fusion peptide (P604-P610) provided by the present invention:

TABLE 2

| Peptide/Fragment | Amino acid sequence | SEQ ID NO |
|---|---|---|
| PEV601 | PESFDGDPASNTAPLQPGGGGGC | 1 |
| PEV602 | RVLQGLPREYVNARHC | 2 |
| PEV603 | YMPIWKFPDEEGAC | 3 |
| PEV604 | PESFDGDPASNTAPLQPRVLQGLPREYVNAR HSLPYMPIWKFPDEEGAC | 4 |
| PEV605 | PESFDGDPASNTAPLQP RVLQGLPREYVNARHS YMPIWKFPDEEGAC | 5 |
| PEV606 | PESFDGDPASNTAPLQP YMPIWKFPDEEGAS RVLQGLPREYVNARHC | 6 |
| PEV607 | RVLQGLPREYVNARHS PESFDGDPASNTAPLQP YMPIWKFPDEEGAC | 7 |
| PEV608 | RVLQGLPREYVNARHS YMPIWKFPDEEGAS PESFDGDPASNTAPLQPC | 8 |
| PEV609 | YMPIWKFPDEEGAS PESFDGDPASNTAPLQP RVLQGLPREYVNARHC | 9 |
| PEV610 | YMPIWKFPDEEGAS RVLQGLPREYVNARHS PESFDGDPASNTAPLQPC | 10 |
| PEV611 | PESFDGDPASNTAPLQP | 12 |

In the individual B cell epitopes PEV611 and PEV601 set out above, PEV601 comprises an additional C-terminal linker ending in Cys not comprised in PEV611. This C-terminal linker in PEV601 itself ends in Cys, which allows this single epitope to be coupled to delivery systems such as virosomes in performing certain of the control experiments set out herein below. When used as part of the fusion peptide of the invention, the B cell epitope in PEV601 is present in this fusion peptide in the form of PEV611 (SEQ ID NO: 12). In the experiments in which PEV601 is employed as a control, it is the portion of PEV601 corresponding to PEV611 (SEQ ID NO: 12) which functions as the B cell epitope.

In a further aspect, the present invention relates to a method of preparing the fusion peptide
I. by a peptide synthesis method comprising
 (i) sequential formation of peptide bonds linking each amino acid to its respectively neighboring amino acid; and
 (ii) Recovering said fusion peptide;
or
II. by a recombinant method comprising the following steps:
 (i) Providing a nucleic acid comprising a nucleic acid sequence encoding a fusion peptide as described above;
 (ii) Transfecting said nucleic acid into a host cell capable of expressing said nucleic acid sequence;
 (iii) Incubating said host cell under conditions suitable for the expression of said nucleic acid sequence; and
 (iv) Recovering said fusion peptide Peptide synthesis methods are known in the art. Reference is made in this regards to "Amino Acid and Peptide Synthesis" (Oxford Chemistry Primers), by John Jones (Author), Oxford University Press. Synthetic peptides can be made by liquid-phase synthesis or solid-phase peptide synthesis (SPPS) on different solid supports (e.g. polystyrene, polyamide, or PEG). There are two majorly used forms of SPPS—F-moc (9H-fluoren-9-ylmethoxycarbonyl) and t-Boc (tert- Butoxycarbonyl). As the skilled person knows, custom peptides are also available from a number of industrial manufacturers, for example Bachem.

It is also known in the art how to prepare nucleic acids encoding a polypeptide sequence of interest based on knowledge of the genetic code, possibly optimizing codons based on the nature of the host cell (e.g. microorganism) to be used in preparing, e.g. expressing and/or secreting the polypeptide. Suitable host cells to this end are also known in the art, and include prokaryotic cells such as e.g. *E. coli* and eukaryotic cells such as e.g. *P. pastoris*. Reference is made in this regard e.g. to the well known lab manual: "Short Protocols in Molecular Biology, 5th Edition, 2 Volume Set: A Compendium of Methods from Current Protocols in Molecular Biology", by Frederick M. Ausubel (Author, Editor), Roger Brent (Editor), Robert E. Kingston (Editor), David D. Moore (Editor), J. G. Seidman (Editor), John A. Smith (Editor), Kevin Struhl (Editor), J Wiley & Sons, London.

In a further aspect, the present invention provides a delivery system associated with a fusion peptide as described above or as obtained or obtainable by a method described above.

As accepted in the art and used herein, a "delivery system" is to be understood as an adjuvant which is particulate, with which the fusion peptide can be associated (covalently and/or non-covalently) and which, in the event of such association, remains so associated under conditions prevailing in vivo. A delivery system promotes and/or effects the conveyance of the fusion peptide to its intended location in viva, e.g. to a B cell, and thus results in a greater amount of fusion peptide reaching cells responsible for the induction of an immune response than if the fusion peptide were to be administered in a form unassociated with the delivery system.

In the event that the fusion peptide is covalently associated with the delivery system, this covalent association takes the form of one or more covalent bonds existing between atoms of the fusion peptide and atoms of the delivery system. The participating atoms in the fusion peptide and the delivery system may be the same element or different elements, the important criterion for classification of the bond as a "covalent bond" being the sharing of pairs of electrons between the respective atoms, or between these atoms and other bonds existing in the fusion peptide and/or delivery system, such that the measure of attraction to repulsion between the respective atoms in the fusion peptide and the delivery system is and remains stable. The form of a covalent bond may vary depending on the electron orbital configuration of the participating atoms, and includes, for example, sigma-bonding, pi-bonding, metal to non-metal bonding and three-center two-electron bonding (i.e. bonds in which two electrons are shared by three atoms, such as agostic interactions between a coordinately unsaturated transition metal and a C—H bond in which two electrons from a C—H bond enter the empty d-orbital of a transition metal and are thereby shared by three atoms). While sigma- and pi-bonding will generally be most common for the purposes of covalently associating a fusion peptide and a delivery system herein, to the extent that a stable and permanent counterbalance between attraction and repulsion of the respective atoms is attained as mentioned above, then any bond having these characteristics is to be understood as a covalent bond which covalently associates the fusion peptide to a delivery system.

In the event that the fusion peptide is non-covalently associated with the delivery system, this non-covalent association will not involve the sharing of pairs of electrons (as above for covalent bonds) but, rather, involves more dispersed types of electromagnetic interactions between one or more atoms of the fusion peptide with one or more atoms of the delivery system. For example, such non-covalent association between the fusion peptide and a delivery system may for example be effected by hydrogen bonding (i.e. the attractive interaction between an already covalently bound H atom with another electronegative atom to which it is not covalently bound), ionic bonding (i.e. the attraction formed between two oppositely charged ions by virtue of this opposite charge), Van der Weals forces (i.e. forces between permanent and/or induced dipoles of existing covalent bonds within the fusion peptide and the delivery system) and/or hydrophobic interactions (forces resulting from the tendency of hydrophobic/aliphatic portions within the fusion peptide described to associate with hydrophobic portions of the delivery system). For example, when the fusion peptide is non-covalently associated with a delivery system which is an emulsion (e.g. Montanide™, discussed in greater detail hereinbelow) the non-covalent association may be effected simply by mixing the fusion peptide with the emulsion. Here, the hydrophobic interactions mentioned above result in the incorporation of the fusion peptide within an oil droplet of the emulsion, with which the fusion peptide will stably remain associated as long it persists together with the emulsion in an aqueous environment. In addition, physical enclosure/encapsulation of the fusion peptide of the invention within the lumen of a delivery system, such as a virosome, a liposome or an ISCOM is also to be understood as a "non-covalent association" in the sense used herein.

When associated with a fusion peptide of the invention, the delivery system can serve several purposes. First, it can shield the fusion peptide from potentially damaging and/or degradative processes in vivo which may otherwise compromise the fusion peptide's ability to elicit the desired immune response before ever reaching a suitable target, e.g. a B cell, Second, certain types of this class of particulate adjuvant are not just passive conveyors of an associated antigenic payload, but also actively promote the uptake of the fusion peptide in an immunogenically relevant manner. For example, a virosome (described in greater detail below) has the potential not only to optimally present a fusion peptide according to the invention to antigen-specific B cells but also bears on its outer surface viral envelope proteins which actively recognize appropriate receptors on the outer surface of immunologically relevant cells, e.g. B cells and antigen presenting cells, and thus actively mediate uptake of the associated fusion peptide within such cells, where the desired immunogenic response is subsequently mounted.

A delivery system may also take the form of another protein or peptide to which the fusion peptide of the invention is bound or fused. In this case, the delivery system does not originate from the ECD of Her2/neu, but is responsible for increasing the strength of the immune response desired therefrom. Known substances in this regard include e.g. tetanus toxoid (TT) polypeptide and keyhole limpet hemocyanin (KLH) polypeptide. It is also contemplated that two or more delivery systems may be effectively used in conjunction, for example a fusion of the fusion peptide according to the invention with e.g. TT to form one polypeptide chain, said polypeptide chain then being encapsulated in or covalently attached to a virosome, and provided in a formulation in this form. In the scenario where the fusion peptide-TT polypeptide is encapsulated in a virosome, the fusion peptide is covalently associated with one delivery system (in this example, TT), while being non-covalently associated with another (in this example, a virosome). In the scenario where the fusion peptide-TT polypeptide is covalently attached to a virosome, the fusion peptide is covalently associated with two different types of delivery system. Such combinations exemplify, in a non-limiting manner, the type of possible associations between the fusion peptide of the invention and one or more of a delivery system as set out above, such associations being encompassed within the meaning of a "delivery system which is covalently and/or non-covalently associated with a fusion peptide".

The delivery system may for example be a virosome, a liposome, a virus-like particle (VLP), tetanus toxoid (TT), a keyhole limpet hemocyanin (KLH), an immunostimulating complex (ISCOM), an emulsion (e.g. incomplete Freund's adjuvant (IFA), a Montanide™, MF59 (Chiron) or IDEC-AF), hepatitis B core antigen (HBO, a nano- or microparticle (e.g. a polylactide co-glycide (PLO) microparticle), an aluminium salt, calcium phosphate, stearyl tyrosine or a viral vector. ISCOMs feature a unique cage-like structure and form spontaneously in an aqueous pseudo-ternary system of phospholipid, cholesterol and quillaja saponin A (QuilA). Montanide™ is a mixture of oil such as mannide oleate and mineral oil and water.

In an especially preferred embodiment, the delivery system is a virosome in which a fusion peptide as described above, or as obtained or obtainable by the above method is encapsulated, or to which a fusion peptide as described above, or as obtained or obtainable by the above method is covalently and/or non-covalently bound. Certain advantages of using virosomes as a delivery system for the fusion peptide of the present invention have been briefly mentioned above and are set out in greater detail below.

Virosomes are an ideal way of presenting immunogenic peptides for recognition by the host Immune system. Further, virosomes containing the desired ratio of one Her2/neu fragment to another can be easily and reliably prepared homogeneously, as the ratio of one fragment to another is set by the makeup of the fusion peptide in which these fragments are comprised, and does not depend on mixing of virosomes containing different Her2/neu ECD fragments.

As used herein, the term "virosome" refers to a vesicle produced by an in vitro procedure that is composed of lipids and at least one viral envelope protein. The lipids are either derived from a biological origin (e.g. eggs, plants, animals, cell cultures, bacteria, viruses) or produced synthetically (chemical synthesis). A virosome may be a reconstituted viral envelope which may be derived from a variety of viruses and which lacks the infectious nucleocapsids and the genetic material of the source virus, e.g. an immunopotentlating reconstituted influenza virosome (IRIV). Thus, a virosome is a special type of lipid vesicle comprising, in its lipid membrane, at least one viral envelope protein.

As used herein, the term "viral envelope protein" refers to any protein encoded by an enveloped virus from which the virosome is partly or completely derived and which is present in the virosomal lipid membrane. Viral envelope proteins sometimes function as "viral fusion proteins", when they play a role in the fusion of viruses or virosomes with target cell membranes. Such "viral fusion proteins" should not be confused with the "fusion peptides" of the present invention. The former mediate the process of fusion, i.e. coalescing, of a virus (or virosome) with a target cell via an appropriate receptor on the surface of the cell, while the latter refer to a fusion, i.e. linking or connection, of at least three B cell epitopes of the ECD of Her2/neu, which in their native state are non-contiguous, into a single polypeptide chain.

Viral envelope protein(s) may be derived from whole virus propagated in bird's eggs or cell culture (e.g. mammalian cells, vertebrate derived cells, insect cells, yeast, plant cells) or produced as recombinant proteins using methods well known to those of skill in the art, provided that the biochemical properties of the protein allow its physical embedment to a lipid membrane. These envelope proteins account for the virosomal functionality, including the ability of virosomes to potentiate the immunogenicity of a comprised fusion peptide. The virosome used in the present invention may also be a chimeric virosome, meaning that it contains viral envelope proteins from at least two different virus strains.

As evidenced by certain of the results shown herein, virosomes have great potential in the design of systems intended to elicit an immunogenic response from a desired substance, e.g. a peptide or protein substance. Furthermore, virosome-based vaccines are expected to be safe, since virosome-based vaccines have already shown a very good safety profile in humans (Glueck, R., Vaccine 1999, 17, 1782).

The virosome may also comprise in its membrane a cationic lipid for effective lyophilisation and reconstitution. In a preferred embodiment, the utilized cationic lipid is a cationic cholesterol derivative, e.g. 3β(N—(N',N',N'-trimethylammonioethane)-carbamoyl)cholesterol chloride (TC-Chol). Such a TC-Chol containing virosome is referred to herein as "TIRIV". In one preferred embodiment, the virosome is a TIRIV or an IRIV. In another embodiment, multiple types of virosomes, e.g. both TIRIV and IRIV may be used together in different ratios as deemed expedient or necessary to e.g. adjust the reconstitutability of the lyophilized product. TIRIV and/or IRIV delivery systems, together with their associated fusion peptides, may also be combined with one or more other non-virosomal delivery systems. Conversely, the fusion peptides may be associated with one or more non-virosomal delivery systems, which is/are then further associated with one or more virosomal delivery systems, e.g. IRIV and/or TIRIV.

While most polypeptide epitopes can be bound to the surface of a virosome, not all will result in constructs suitable for use as the active agents in Her2 vaccines. For example, certain polypeptides, when conjugated to the surface, result in an increased propensity of the so-conjugated virosomes to disadvantageously aggregate. However, the present inventors have found that the fusion peptides according to the invention can be bound to virosomes such as e.g. a TIRIV, and that such virosomes subsequently show superior characteristics such as stability and polydispersity. The polydispersity of a virosomal preparation is an indication for the homogeneity of the particle size in an aqueous solution, with lower polydispersity being associated with a greater degree of homogeneity of size over all virosomes present in the composition. Such virosome-coupled fusion peptides also exhibit a potentiated immune response. Certain chemico-physical characteristics of certain embodiments of the fusion peptide of the invention are for example summarized in the following table (Table 3):

TABLE 3

| Parameter | PEV601 | PEV602 | PEV603 | PEV604 | PEV605 | PEV606 | PEV607 | PEV608 | PEV609 | PEV610 |
|---|---|---|---|---|---|---|---|---|---|---|
| Solubility(I)IRIV (mg/ml) | 2-3 | 0.5 | 2-3 | 0.5-1.5 | no data | no data | 0.5-1.5 | no data | no data | no data |
| Stabilty(I)IRIV | acceptable | limited | limited | limited | limited | limited | limited | limited | limited | limited |
| pI | 3.5 | 9.5 | 4.1 | 4.7 | 4.7 | 4.7 | 4.7 | 4.7 | 4.7 | 4.7 |

TABLE 3-continued

| Parameter | PEV601 | PEV602 | PEV603 | PEV604 | PEV605 | PEV606 | PEV607 | PEV608 | PEV609 | PEV610 |
|---|---|---|---|---|---|---|---|---|---|---|
| Solubility TIRIV (mg/ml) | 2-3 | 0.5 | <0.2 | 0.8 | 0.8 | 0.8 | 0.8 | 0.8 | 0.8 | 0.8 |
| Polydispersity of TIRIV (with mean diameter) | 0.15 (185 nm) | 0.22 (190 nm) | no integration | 0.15 (167 nm) | 0.32 (230 nm) | 0.07 (165 nm) | 0.18 (175 nm) | 0.07 (167 nm) | 0.17 (202 nm) | 0.20 (223 nm) |

The table demonstrates that fusion of the individual epitopic peptide fragments PEV601, PEV602 and PEV603 into various fusion peptides results, among other things, in a very uniform pI value for the resulting fusion peptides as compared to the corresponding values observed for each of the constituent peptide fragments. This greatly simplifies coupling of the fusion peptides to delivery systems such as e.g. virosomes and/or TT.

In another aspect, the present invention provides a fusion peptide as described above or a delivery system covalently and/or non-covalently associated with the above described fusion peptide for use as a medicament. In a preferred embodiment, the medicament is a vaccine, in a related aspect, the present invention relates to a composition comprising a fusion peptide according to the invention and/or a delivery system covalently and/or non-covalently associated with a fusion peptide according to the invention. In a preferred embodiment, this composition is a pharmaceutical composition and additionally comprises a pharmaceutically acceptable carrier (e.g. excipients, diluents, etc.). In an especially preferred embodiment, the pharmaceutical composition is a vaccine composition.

Any of the above types of compositions or medicaments may comprise a delivery system with which the fusion peptide described hereinabove is covalently and/or non-covalently associated in the above manner.

Further, any of the above types of compositions or medicaments may comprise an immunopotentiator instead of or in addition to a delivery system as mentioned above.

As used herein, the term “immunopotentiator” refers to any of a class of adjuvant substances included in a composition which increase the magnitude of the immune response elicited by the fusion peptide beyond that which would be expected, either from the fusion peptide alone or from the fusion peptide associated with a delivery system as defined hereinabove in the absence of such an immunopotentiator. Many of the immunopotentiators activate the cells through interaction with their receptors, including the pathogen-recognition receptors (PRR). Unlike a delivery system, an Immunopotentiator is non-particulate, and as such exists in solubilized form in solution with the fusion peptide, or with the fusion peptide as associated with a particulate delivery system. In some cases it is especially preferred to combine, in the same composition, pharmaceutical composition, vaccine composition, medicament or vaccine, one or more delivery systems with one or more immunopotentiators, in order to maximize the magnitude of the obtainable immune response. However, this need not be the case, and it is also contemplated to employ a fusion peptide with only an immunopotentiator.

The immunopotentiator may be chosen from one or more of any of known substances or substance groups, such as for example a bacterial toxin (e.g. *E. coli* type II heat-labile enterotoxin (HLT), cholera toxin (CT)), a bacterial cell-surface lipopolysaccharide (LPS), lipid A and/or a synthetic derivative thereof, an oligopeptide (e.g. muramyl dipeptide (MOP), muramyl tripeptide and/or synthetic derivatives thereof), an alternative pathogen-associated molecular pattern (PAMP; e.g., flagellin), a lipopeptide (e.g. MALP-2), a lipoprotein, a peptidoglycan, lipoteichoic acid (LTA), a yeast cell wall component, a glycolipid (e.g. lipoarabinomannan), viral or bacterial DNA, an oligonucleotide (e.g. CpG, etc.), double-stranded RNA, polyinosinic-polycytidylic acid (poly I:C), single-stranded viral RNA, a small molecule immune potentiator (SMIP; e.g. resiquimod, imiquimod), a cytokine (e.g. Interleukin-2 (IL-2), IL-12, GM-CSF, etc.), a chemokine (e.g. RANTES), a saponin (e.g. Quils, QS-21 (SmithKline Beecham)), a polyphosphazene, a cochleate structure, a suppressor of cytokine signalling small interfering RNA (SOCS sIRNA), or a Pan DR epitope (PADRE). Of course, mixtures of two or more of the above within the same composition, pharmaceutical composition, vaccine composition, medicament or vaccine, either alone or with one or more delivery systems as defined herein above, are also contemplated.

In another aspect, the present invention relates to the use of a fusion peptide according to the invention, optionally associated with a delivery system and/or together with an immunopotentiator as described above, for preparing a composition and/or a medicament for the prevention, treatment and/or amelioration of a cancer characterized by expression or over-expression of Her2. In a preferred embodiment, the composition is a pharmaceutical composition and may additionally comprise a pharmaceutically acceptable carrier. In an especially preferred embodiment, the pharmaceutical composition and/or medicament is a vaccine composition.

A further aspect of the invention provides a method of preventing, treating and/or ameliorating a cancer characterized by expression or over-expression of Her2 in a patient in need or suspected need thereof, comprising the step of administering to said patient an effective amount of a fusion peptide as described above, a fusion peptide obtainable according to a method as described above and/or either of such fusion peptides covalently and/or non-covalently associated to a delivery system as described above. The fusion peptide can be administered either alone or in covalent and/or non-covalent association with a delivery system as described hereinabove. The fusion peptide, either alone or in association with a delivery system, may be present in a composition, a pharmaceutical composition, a vaccine composition, a medicament or a vaccine as described above, and the composition, pharmaceutical composition, vaccine composition, medicament or vaccine may additionally comprise an immunopotentiator as described above.

In a preferred embodiment, the cancer characterized by expression or over-expression of Her2/neu is chosen from breast cancer, ovarian cancer, endometrial cancer, gastric cancer, pancreatic cancer, prostate cancer and salivary gland cancer. Especially preferred, the cancer characterized by expression or over-expression of Her2/neu is breast cancer.

As used herein, the terms “administration” or “administering” refer to introducing a fusion peptide according to the invention or a fusion peptide-containing composition or medicament or vaccine composition of the invention, including those in which the fusion peptide is comprised in a virosome, into a patient’s body so that the patient’s immune system mounts a response to the multiple Her2 epitopes comprised in the fusion peptide. As used herein, a "patient in need thereof" includes an individual who has been diagnosed with cancer over expressing the Her2 protein. It also includes individuals who have not yet been diagnosed with cancer, including but not limited to individuals who have not presented with any symptoms, but who for example have a family history and therefore a suspected genetic predisposition to develop cancer over-expressing Her2. In its broadest sense, then, the term "a patient in need thereof" encompasses individuals with an already present need as well as those in which a need is suspected or anticipated in the future.

As the terms used herein, a medicament which "prevents" cancer will reduce the risk, ideally down to zero, to develop cancer. Furthermore, this term also refers to the prevention of re-development of cancer, e.g. following surgery of a primary tumor. A medicament which "treats" cancer will eliminate the disease altogether by eliminating its underlying cause so that, upon cessation of administration of the fusion peptide, the disease does not re-develop but remains in remission. A medicament which "ameliorates" cancer does not eliminate the underlying cause of the disease, but reduces the severity of the disease as measured by any established grading system and/or as measured by an improvement in the patient's well-being, e.g. decrease in pain and discomfort. An "effective amount" is an amount of a pharmaceutical preparation that alone, or together with further doses according to an established dosing regimen, effects the desired prevention, treatment or amelioration as defined above.

As used herein, the term "vaccine" refers to an antigenic preparation used to engender immunity to a disease or an ability to combat disease by conferring on the immune system the ability to recognize and specifically eliminate cells associated with the disease. Vaccines can be prophylactic (e.g. to prevent the development of a disease not yet manifested), therapeutic (to treat or eliminate an already manifested disease) or palliative (to ameliorate an already manifested disease). The intended meanings of these terms are explained hereinabove.

Such a vaccine comprising a fusion peptide of the present invention as the principal or partial active ingredient, can be administered in a wide variety of therapeutic/prophylactic dosage forms in the conventional vehicles for topical, mucosal, systemic, and local administration.

Thus, the invention provides compositions for parenteral administration which comprise a solution of a fusion peptide optionally in combination with one or more of a suitable immunopotentiator as described above and/or one or more of a suitable delivery system in an acceptable carrier, preferably an acceptable aqueous carrier. A variety of aqueous (pharmaceutically acceptable) carriers may be used, e.g. water, buffered water, 0.4% saline, 0.3% glycine, hyaluronic acid and the like. These compositions may be sterilized by conventional, well known sterilization techniques or may be sterile-filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions, such as pH-adjusting and buffering agents, tonicity-adjusting agents, wetting agents and the like, for example sodium acetate, sodium lactate, sodium chloride, potassium chloride, calcium chloride, sorbitan monolaurate, triethanolamine oleate, sucrose or other carbohydrates, among many others. Actual methods for preparing parenterally administrable compounds will be known or apparent to those skilled in the art and are described in more detail in for example, Remington: The Science and Practice of Pharmacy ("Remington's Pharmaceutical Sciences") Gennaro A R ed. 20th edition, 2000: Williams & Wilkins P A, USA, which is incorporated herein by reference.

The route and regimen of administration will vary depending upon the stage or severity of the condition to be treated, and is to be determined by the skilled practitioner. For example, a fusion peptide according to the present invention, a delivery system as described above and/or compositions comprising said fusion peptide and/or said delivery system as described above may be used for preparing a pharmaceutical composition or medicament that can be administered in subcutaneous, intradermal, intralymphatic or topical or mucosal (nasal), or intramuscular form. All of these forms are well known to those of ordinary skill in the pharmaceutical arts.

Advantageously, suitable formulations of the present invention may e.g. be administered in a single dose, which may be repeated daily, weekly or monthly. Furthermore, compounds of the present invention, particularly those containing virosomes or liposomes, can be administered in intramuscular, subcutaneous, intralymphatic intranasal or intravaginal form, or via transdermal routes known to those of ordinary skill in the art. To be administered in the form of a transdermal delivery system, the dosage administration will generally be continuous rather than intermittent throughout the dosage regimen.

The prophylactic or therapeutic medicaments of the present invention are for administration in pharmaceutically acceptable preparations. In addition to the immunopotentiators described above, such preparations may routinely contain pharmaceutically acceptable concentrations of salt, buffering agents, preservatives, compatible carriers (as described above) and optionally other therapeutic agents.

The preparations of the invention are administered in effective amounts. An effective amount is that amount of a pharmaceutical preparation that, alone or together with further doses, stimulates the desired response. Generally, doses of fusion peptides ranging from 0.01 µg/kilogram to 500 µg/kilogram body weight, depending upon the mode of administration, are considered effective. The preferred range is believed to be between 0.1 µg/kilogram and 10 µg/kilogram body weight. The absolute amount will depend upon a variety of factors, including the composition selected for administration, whether the administration is in single or multiple doses, and individual patient parameters including age, physical condition, size, weight, and the stage of the disease. These factors are well known to those of ordinary skill in the art and can be routinely addressed.

The dosage regimen utilizing the compositions of the present invention is selected in accordance with a variety of factors, including for example age, weight, and medical condition of the patient, the stage and severity of the condition to be treated, and the particular fusion peptide intended for administration. A physician of ordinary skill can readily determine and prescribe the effective amount of e.g. a fusion peptide-containing medicament required to prevent, treat or ameliorate the progress or severity of a malignancy. Optimal precision in achieving concentration of active agent with the range that yields efficacy either without toxicity or with no more than acceptable toxicity requires a regimen based on the kinetics of the agent's availability to target sites. This process involves a consideration of the distribution, equilibrium, and elimination of the active agent, e.g. the fusion peptide of the invention, and is within the ability of the skilled practitioner.

In the uses of the present invention, the fusion peptide and/or delivery system described herein in detail can form the active agent and are typically administered in admixture with suitable pharmaceutical carriers such as diluents or excipients which are suitably selected with respect to the intended form of administration, e.g. oral tablets, capsules, elixirs, syrups, and the like, and consistent with conventional pharmaceutical practices. When desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethyl cellulose, polyethylene glycol, waxes and the like. Lubricants used in these dosage forms include, without limitation, sodium oleate, sodium stearate, magnesium stearate, sodium benzoate, sodium acetate, sodium chloride and the like. Dis-Integrators include, without limitation, starch, methyl cellulose, agar, bentonite, xanthan gum and the like.

For parenteral administration, sterile suspensions and solutions are desired. Physiological preparations which may contain suitable preservatives are employed when intramuscular or subcutaneous or intradermal administration is desired.

As discussed above, subjects may receive an administration of an effective amount of a fusion peptide in a form covalently and/or non-covalently associated with one or more delivery systems such as a virosome and/or one or more additional adjuvants such as an immunopotentiator as defined above, although administration of fusion peptides by themselves is also contemplated. Alternatively, another example of a delivery system is a liposome. Liposomes may e.g. be formed from a variety of compounds, including for example cholesterol, stearylamine, and various phosphatidylcholines.

Initial doses of the fusion peptide of the invention or corresponding delivery systems such as e.g. a virosome can be followed by booster doses, following immunization protocols standard in the art. For such booster doses, the immunostimulatory effects of e.g. the substances of the instant invention may be further increased in the same manner as described above for the initial dose, e.g. by combining a substance of the present invention with e.g. one or more adjuvants such as one or more immunopotentiators as defined hereinabove.

The present invention is not to be limited in scope by the specific embodiments described herein. Indeed, various modifications of the invention in addition to those described herein will become apparent to those skilled in the art from the foregoing description, as well as from the examples. Such modifications are intended to fall within the scope of the appended claims.

EXAMPLES

The following examples are provided to better illustrate the claimed invention and are not to be interpreted as limiting the scope of the invention. To the extent that specific materials are mentioned, this is merely for purposes of illustration and is not intended to limit the invention. Unless otherwise specified, biochemical and molecular biology procedures, such as those set forth in Voet, *Biochemistry*, Wiley, 1990; Stryer 1995; *Peptide Chemistry. A Practical Textbook*, 2nd ed., Miklos Bodanszky, Springer-Verlag, Berlin, 1993; Sambrook et al., Molecular Cloning, Cold Spring Harbor Laboratory (2001), Ausubel et at (Eds.) Current Protocols In Molecular Biology, John Wiley & Sons (2000) are used. One skilled in the art may develop equivalent means or reactants without the exercise of inventive capacity and without departing from the scope of the invention. It will be understood that many variations can be made in the compositions and procedures herein described while still remaining within the bounds of the present invention. Likewise, it is understood that, due to known structural or chemical similarities such as polarity, bulk, or orientation between amino acid side chains, peptide sequences with amino acids or replacement structures equivalent to those disclosed herein will retain similar function. It is the intention of the inventors that such variations are included within the scope of the invention.

Example 1

Materials

Octaethyleneglycol-mono-(n-dodecyl)ether (OEG, C12E8) was purchased from Sigma (Buchs, Switzerland), respectively. Sucrose (Eur. Phar.) is purchased from Merck (Dietikon, Switzerland). Egg phosphatidyl choline (PC) is obtained from Lipoid (Cham, Switzerland). 1-Oleoyl-3-palmitoyl-rac-glycero-2-phosphoethanolamine (PE) is obtained from Bachem (Bubendorf, Switzerland). Bio-Beads SM2 are purchased from Bio-Rad Laboratories (Glattbrugg, Switzerland). 1,2-Dipalmiloyl-sn-glycero-3-phosphoethanolamine-N-[4-(p-maleimidomethyl)cyclohexane-carboxamide] (N-MCC-PE) is purchased from Genzyme Pharmaceutical (Liestal, Switzerland). Cholesteryl N-(trimethylammonioethyl)carbamate chloride (TC-chol) is purchased from Merck Eprova (Schaffhausen, Switzerland). Montanide ISA™ 51 (a water/oil emulsion analogous to Incomplete Freund's adjuvant FA, but containing a more refined mineral oil than incomplete Freund's adjuvant (Handbook of cancer vaccines, 2004, Eds. Michael A. Morse, Timothy M. Clay, H. Kim Lyerly; Springer-Verlag Berlin) is purchased from Seppic, France and ISCOMs AbISCO®-100 from Isconova, Sweden Example 2

2.1 Synthesis of Peptides and Fusion Peptides

Peptides were chemically synthesized at Bachem AG (Bubendorf, Switzerland) or at GL Biochem Ltd. (Shanghai, China) with an HPLC purity >90%. Peptides were analyzed by mass spectrometry to confirm the expected molecular mass.

Example 3

Analysis by Western Blot

Samples to be analyzed by SDS-PAGE were mixed with the appropriate sample buffer supplied by Invitrogen (Basel, Switzerland) with or without reducing agent (Invitrogen) and incubated at 85° C. for 2 minutes. 5-10 µl of the sample were applied on a polyacrylamide gel (Invitrogen, Basel, Switzerland) and run according to the manufacturer's instruction. Gels were either further analyzed by Western blot analysis and/or stained by silver using the SilverQuest Kit (Invitrogen, Basel, Switzerland) following the "fast staining" protocol supplied by the manufacturer.

Gels were transferred onto a nitrocellulose membrane with the iBlot instrument (Invitrogen, Basel, Switzerland) according the manufacturer's instructions. The membrane was washed briefly in PBS containing 0.2% Tween 20 and unspecific binding of antibodies or sera was blocked by incubation with 5% Milk in PBS for 2 h. After washing membranes again in PBS/0.2% Tween 20, blots were incubated with first antibody/serum diluted in 0.5% Milk in PBS/0.2% Tween 20 1:100 up to 1:10000 depending on the antibody at RT for 1-2 h. Membranes were washed 3 times for 5 minutes in PBS/

0.2% Tween 20 and incubated in appropriate horseradish-peroxidase (HRP)-labeled secondary antibody diluted 1:1'000 up 1:20'000 in 0.5% Milk in PBS/0.2% Tween 20. After washing the membranes for 5 times in PBS/0.2% Tween 20, visualization was done by chemiluminescence using SuperSignal West Dura kit (Pierce, Lausanne, Switzerland) according to manufacturer's instruction.

Example 4

Standard Methods as Used in the Following Experiments
4.1 Immunogenicity of Fusion Peptides
4.1.1 Animals
Female Balb/c mice (6-8 weeks at start of experiment) were used throughout this study. Mice were housed in appropriate animal care facilities and handled according to international guidelines.
4.1.2 Immunization of Mice
Balb/c mice were immunized subcutaneously with 1 µg HA of inactivated influenza A/H1N1 virus. Three weeks later the mice were immunized twice with vaccine formulations in a 3 week interval. Blood was collected 2 weeks after the final inoculation and sera were tested in ELISA.
4.2 ELISA to Detect Abs Against—Peptide Epitopes
Polysorp plates (Nunc) were coated overnight at 4° C. with 100 µl of a 10 µg/ml solution of the peptide-phosphatidyle-thanolamine conjugate PEV601 (SEQ ID NO: 1)-PE, PEV602 (SEQ ID NO: 2)-PE, or PEV603 (SEQ ID NO: 3)-PE in PBS (pH 7.4). Wells were then blocked with 5% milk powder in PBS for 2 h at RT, followed by three washes with PBS containing 0.05% Tween 20. Plates were then incubated with serial dilutions of the mouse serum in PBS containing 0.05% Tween 20 and 0.5% milk powder for 2 h at 37° C. After being washed, plates were incubated with HRP-conjugated goat anti-mouse Ig antibody (BD Bioscience) for 1 h at 37° C. After being washed again, OPD-substrate (O-phenylendi-amine tablets, Fluke) was added, and the plates were incubated in the dark at room temperature until the colorimetric reaction had progressed sufficiently and reaction was stopped by addition of 100 µl 1 M $H_2SO_4$ and optical densities (OD) were read at 492 nm on a Spectra Max Plus (Molecular Devices).

Example 5

Fusion Peptides Induce Higher Antibody Levels Against a Single B Cell Epitope Than Inducible by the Respective B Cell Epitope Alone It was desired to investigate the strength of the immune response attributable to a single epitope (i.e. a single fragment of the ECD of Her2/neu) as elicited in the context of a fusion peptide according to the invention compared to that elicited using the single epitope alone Balb/c mice were immunized subcutaneously with 1 µg HA of inactivated influenza A/H1N1 virus. Three weeks later each respective mouse was immunized subcutaneously with PEV601 (SEQ ID NO: 1), PEV602 (SEQ ID NO: 2), PEV603 (SEQ ID NO: 3), PEV604 (SEQ ID NO: 4), PEV605 (SEQ ID NO: 5), PEV606 (SEQ ID NO: 6), PEV607 (SEQ ID NO: 7), PEV608 (SEQ ID NO: 8), PEV609 (SEQ ID NO: 9), or PEV610 (SEQ ID NO: 10) coupled to virosomes (IRIV) twice within 3-week interval. Blood was collected 2 weeks after the final inoculation and sera were tested in ELISA using a respective single epitope comprised in the fusion peptide. Representative results are shown in FIG. 1 for the ELISA performed using the single epitope PEV603 (SEQ ID NO: 3)

More specifically for FIG. 1, this figure demonstrates that fusion peptides according to the invention induce higher antibody levels against a given epitope than induced by a single peptide containing only that epitope. The antibody levels were measured by ELISA performed on serum obtained from individual mice immunized with the substances Indicated in the figure. ELISA plates were coated with PEV603 (SEQ ID NO: 3). The presence of antibody specifically binding to PEV603 in serum is expressed as absorbance (OD) at 492 nm. Absorbance curves obtained using sera from mice immunized with virosomes (specifically, IRIV) comprising fusion peptides according to the invention (comprising multiple epitopes) are solid, while the curve obtained using serum from mice immunized with the single-epitope peptide fragment PEV603 is dashed. As can be seen in the figure, the antibody response against PEV603 is higher when PEV603 is incorporated as one of several fragments in a fusion peptide on a single polypeptide chain. This indicates that fusion of a single given fragment, i.e. a single given B cell epitope, to other fragments within a single polypeptide chain can elicit a more potent antibody response against this given epitope than elicited by that epitope alone. The data points obtained at serum dilution 1:100 (arrow at top left of FIG. 1) were then used to generate FIG. 2C, as described in more detail below.

Figure 2:
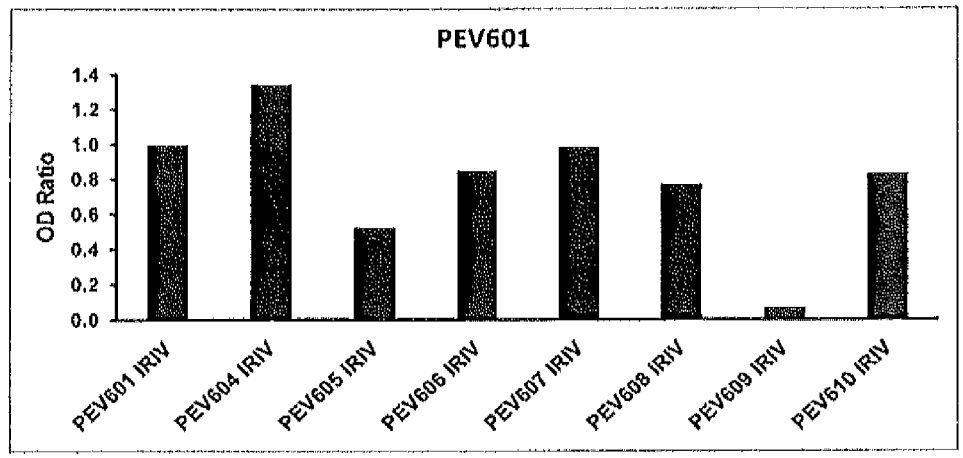
FIG. 2 Relative antibody responses to the individual peptide fragments PEV601 (SEQ ID NO: 1; A), PEV602 (SEQ ID NO: 2; B) and PEV603 (SEQ ID NO: 3; C) when administered to mice alone (leftmost bar in each of FIG. 2A-2C) or as part of fusion peptides of the invention PEV604 (SEQ ID NO: 4), PEV605 (SEQ ID NO: 5), PEV606 (SEQ ID NO: 6), PEV607 (SEQ ID NO: 7), PEV608 (SEQ ID NO: 8), PEV609 (SEQ ID NO: 9) and PEV610 (SEQ ID NO: 10). Observed antibody responses have in each case been normalized relative to those obtained for the respective single epitope.
Figure 2:
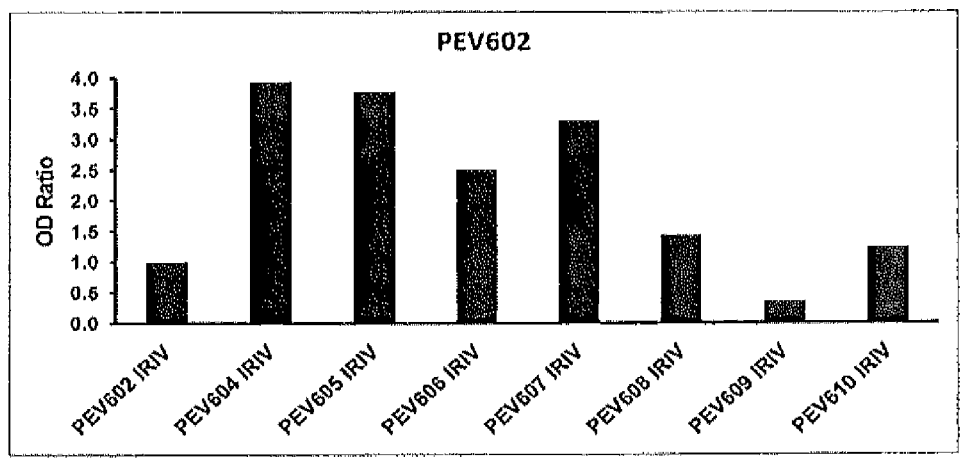
Figure 2:
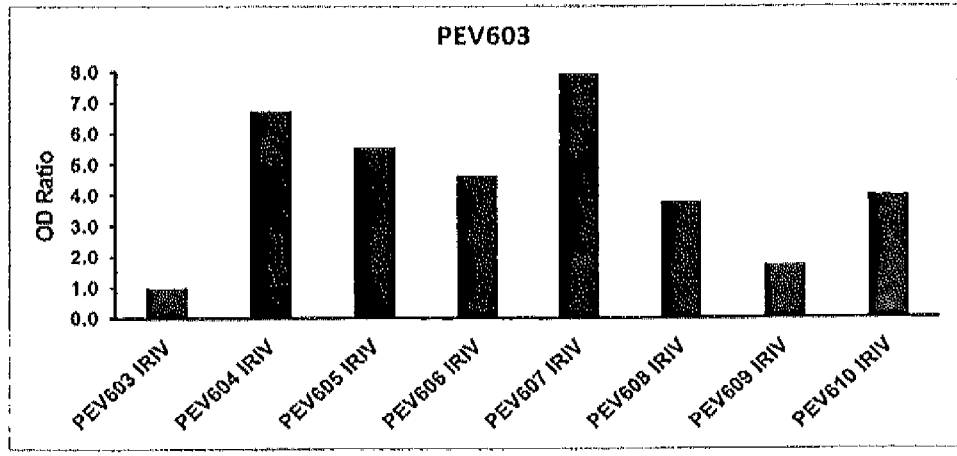

The data of FIG. 1 are representative data for the immune response against the single epitope, i.e. single ECD fragment PEV603 (SEQ ID NO: 3), both alone and in the larger context of a fusion peptide of the invention. Similar experiments were performed to investigate the immune response elicited by the respective single B cell epitopes PEV601 (SEQ ID NO: 1) and PEV602 (SEQ ID NO: 2), both alone and as part of a fusion peptide of the invention. The data from all these experiments (at serum dilution 1:100; arrow at top left of FIG. 1) is shown in FIG. 2 as antibody responses relative to the immune response to the respective fragment PEV601 (SEQ ID NO: 1; FIG. 2A), PEV602 (SEQ ID NO: 2; FIG. 2B) or PEV603 (SEQ ID NO: 3; FIG. 2C) alone, which in each case has been normalized to a value of 1.0 (leftmost data bar in respective FIGS. 2A, 2B and 2C). The subsequent data bars progressing to the right of each of FIGS. 2A, 2B and 2B show the relative of the magnitude of the antibody response to the epitope PEV601, PEV602 and PEV603, respectively, when each respective fragment is part of fusion peptides of the invention PEV604 (SEQ ID NO: 4), PEV605 (SEQ ID NO: 5), PEV606 (SEQ ID NO: 6), PEV607 (SEQ ID NO: 7), PEV608 (SEQ ID NO: 8), PEV609 (SEQ ID NO: 9) and PEV610 (SEQ ID NO:10). As can clearly be seen in FIG. 2, the magnitude of the antibody response to each of these three fragments is in most cases greater than that observed when administering the respective fragment alone, outside of the context of the fusion protein of the invention.

Figure 3:
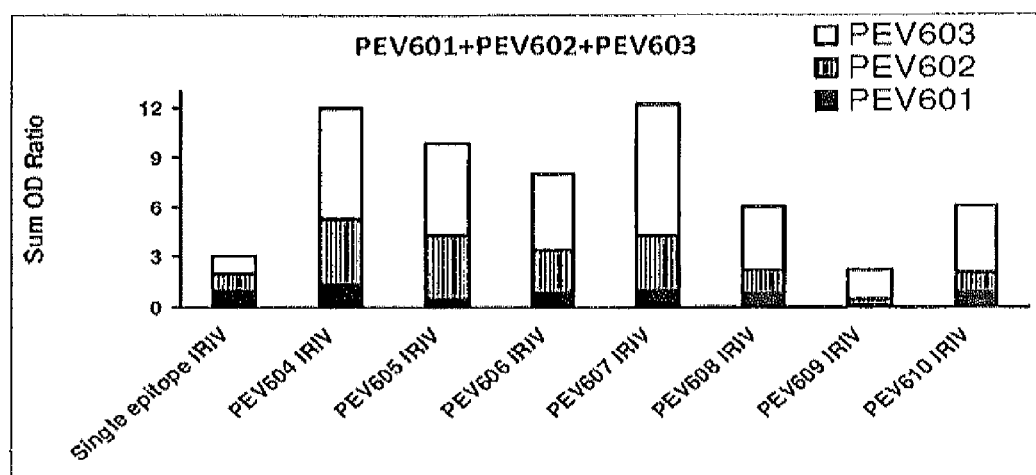
FIG. 3 Sums of normalized OD ratios attributable to each of epitopes PEV601 (SEQ ID NO: 1; white), PEV602 (SEQ ID NO: 2; hatched) and PEV603 (SEQ ID NO: 3; black) depicted in FIG. 2A-C when administered alone (leftmost bar) or together in fusion peptides according to the invention. The "sum" antibody response to any given fusion peptide may be seen as analogous to the total immunogenic response due to all B cell epitopes in vivo. While the antibody response attributable to a given epitope within a fusion peptide is in some cases less than observed with the respective fragment alone, the sum total of normalized antibody responses over all peptide fragments within a given fusion peptide is in almost all cases significantly higher than what would be expected as the simple addition sum of the corresponding single epitope components. As compared to the antibody response attributable to single epitopes, the combination of multiple single B cell epitopes into a fusion peptide according to the invention thus results in a synergistic potentiation of the overall antibody response.

FIG. 3 is a cumulative interpretation of the data presented in FIG. 2. In FIG. 3, the data of FIG. 2 is presented as sums of normalized OD ratios attributable to each of fragments PEV601 (SEQ ID NO: 1; white), PEV602 (SEQ ID NO: 2; hatched) and PEV603 (SEQ ID NO: 3; black) depicted in FIG. 2A-C when administered alone (leftmost bar of FIG. 3) or together in various fusion peptides according to the invention (7 data bars to the right). The "sum" antibody response to any given fusion peptide may be seen as analogous to the cumulative immunogenic response collectively elicited by all epitopic peptide fragments in vivo when contained in a fusion peptide according to the invention. While the antibody response attributable to a given individual epitopic fragment within a fusion peptide is in some cases less than that observed with the respective fragment alone, the collective response attributable to the sum total of antibody responses over all epitopic peptide fragments within a given fusion peptide is in almost all cases significantly higher than what would be expected as the simple addition sum of the corresponding single fragment components (represented in FIG. 3 by the leftmost column, showing the sum of normalized single fragment immune responses as 1+1+1=3). As compared to the antibody response attributable to single epitope fragments, the combination of multiple single epitope fragments into a fusion peptide according to the invention therefore results in a synergistic potentiation of the overall antibody response beyond what would be expected based on the arithmetic sum of constituent parts in any given fusion peptide.

Example 6

Fusion Peptides Can be Coupled to (i.e. Covalently Associated with) Various Delivery Systems: Comparison of Virosomes (IRIV) and Tetanus Toxoid (TT)

Figure 4:
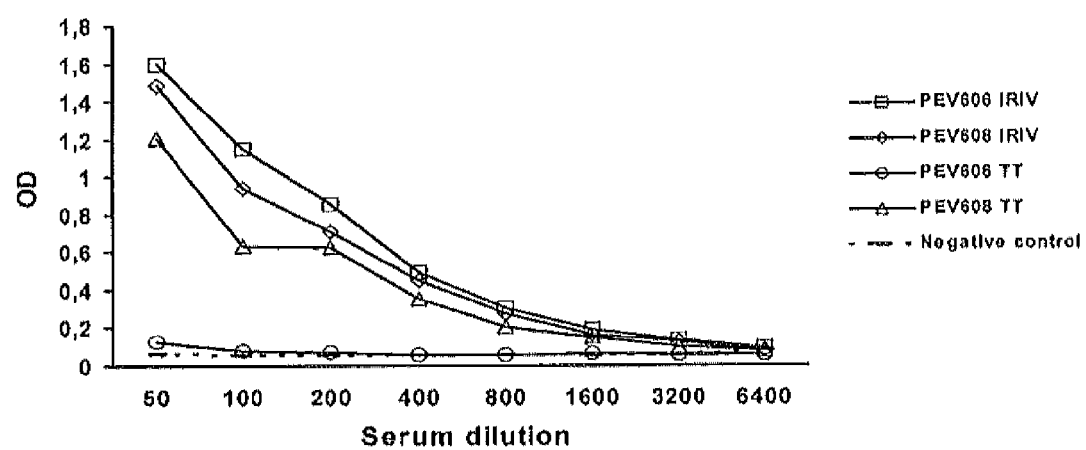
FIG. 4 Demonstration that fusion peptides PEV606 (SEQ ID NO: 6) and PEV608 (SEQ ID NO: 8) coupled to a virosome (IRIV) delivery system induce higher antibody levels against a single peptide epitope (PEV603; SEQ ID NO: 3) than when coupled to a tetanus toxoid (TT) delivery system. The antibody levels were measured by ELISA performed on sera obtained from mice immunized with the formulations indicated in the figure. ELISA plates were coated with PEV603 (SEQ ID NO: 3). The presence of antibody in serum is expressed as absorbance (OD) at 492 nm.

It was desired to compare the effect of delivery systems on the immunogenic response which can be elicited by selected fusion peptides according to the invention. To this end, Balb/c mice were immunized subcutaneously with 1 µg HA of inactivated influenza A/H1N1 virus. Three weeks later the mice were immunized subcutaneously with PEV606 (SEQ ID NO: 6) and PEV608 (SEQ ID NO: 8), coupled to (i.e. covalently associated with) either virosomes (IRIV) or tetanus toxoid (TT) twice with a 3-weeks interval. Blood was collected 2 weeks after the final inoculation and sera were tested in ELISA. ELISA plates were coated with PEV603 (SEQ ID NO: 3). The presence of antibody in serum is expressed as absorbance at 492 nm. The results are shown in FIG. 4. The data shown in FIG. 4 demonstrate that fusion peptides PEV606 (SEQ ID NO: 6) and PEV608 (SEQ ID NO: 8) coupled to a virosome (IRIV) delivery system induce higher antibody levels against a single peptide epitope (PEV603; SEQ ID NO: 3) comprised in the fusion peptides than when coupled to a tetanus toxoid (TT) delivery system. The antibody levels were measured by ELISA performed on sera obtained from mice immunized with the formulations indicated in the figure.

Example 7

Fusion Peptides Can be Associated with Various Delivery Systems

Comparison of Virosomes (IRIV), Montanide™ and ISCOM Delivery Systems

Figure 5:
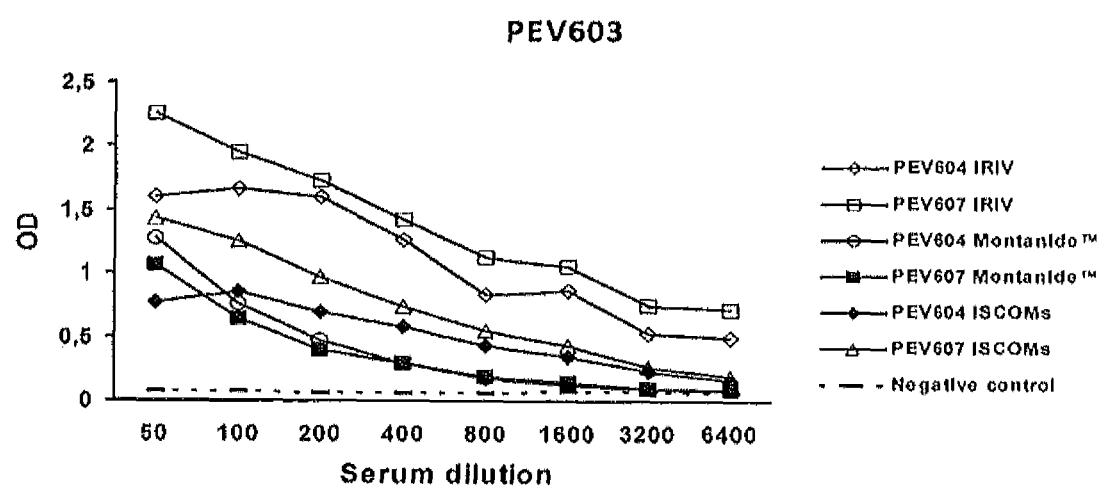
FIG. 5 Demonstration that fusion peptides PEV604 (SEQ ID NO: 4) and PEV607 (SEQ ID NO: 7) in formulations with virosome delivery systems induce higher antibody levels against a single B cell epitope (PEV603; SEQ ID NO: 3) than corresponding formulations with Montanide™ or ISCOM delivery systems. The antibody levels were measured by ELISA performed on sera obtained from mice immunized with the formulations indicated in the figure. ELISA plates were coated with PEV603 (SEQ ID NO: 3). The presence of antibody in serum is expressed as absorbance (OD) at 492 nm.

Balb/c mice were immunized subcutaneously with 1 µg HA of inactivated influenza A/H1N1 virus. Three weeks later the mice were immunized subcutaneously with PEV606 (SEQ ID NO: 6) and PEV608 (SEQ ID NO: 8), coupled to either virosomes (IRIV) or formulated with Montanide ISA™ 51 (Montanide ISA™ 51 is mannide oleate- and mineral oil-water emulsion) or ISCOMs twice with a 3-weeks interval. Blood was collected 2 weeks after the final inoculation and sera were tested in ELISA. The antibody levels were measured by ELISA performed on sera obtained from mice immunized with the formulations indicated in the figure. ELISA plates were coated with PEV603 (SEQ ID NO: 3). The presence of antibody in serum is expressed as absorbance at 492 nm. The results are shown in FIG. 5. The data shown in FIG. 4 demonstrate that fusion peptides PEV604 (SEQ ID NO: 4) and PEV607 (SEQ ID NO: 7) coupled to a virosome delivery system induce higher antibody levels against a single epitope (PEV603; SEQ ID NO: 3) than corresponding fusion peptides formulated with a Montanide™ or ISCOM delivery system.

Example 8

Coupling Fusion Peptide to Phosphoethanolamine

For a virosomal preparation of 4 ml, the designated amount of the fusion peptide is provided and resuspended in 1 ml of 100 mM OEG in PBS. This solution is transferred to 50 mg immobilized Tris-(2-carboxyethyl) phosphine (TCEP) on Amberilie Beads (Merck Biosciences Novabiochem, Laeufeltingen, Switzerland) and incubated for 30 min at RT. The beads are removed and the solution is transferred to 4 mg of fresh N-MCC-PE (ca. 4.3 µmol; Genzyme Pharmaceuticals, Liestal, Switzerland) and incubated at 25° C. while shaking for at least 2 h. Finally, unused maleimide groups in the phosphoethanolamine are consumed by the addition of trace amounts of Tris buffer pH 7.4. The solution is stored at 4° C. until use.

Example 9

Vaccine Composition Containing Fusion Peptide in Combination with a Virosome Delivery System 9.1 Reagents Used in Preparation and Working Examples
Reagents: Octaethyleneglycol-mono-(n-dodecyl)ether (OEG, $C_{12}E_8$), was purchased from Fluke Chemie GmbH-(Buchs, Switzerland). Sucrose (Eur. Phar.) was purchased from Merck (Dietikon, Switzerland). Egg phosphatidyl choline (PC) was obtained from Lipoid (Cham, Switzerland), 1-Oleoyl-3-palmitoyl-rac-glycero-2-phosphoethanolamine was obtained from Bachem (Bubendorf, Switzerland). Bio-Beads SM2 were purchased from Bio-Rad Laboratories (Glattbrugg, Switzerland). Cholesterol N-(trimethylammonloethyl)carbamate chloride (TC-chol) was purchased from Merck Eprova (Schaffhausen, Switzerland). Influenza viruses of the A/Singapore/6/86 (A/Sing) strain and other influenza A strains, propagated in the allantoic cavity of embryonated eggs (Gerhard, W. (1976), J. Exp. Med. 144: 985-995), were obtained from Berna Biotech AG (Bern, Switzerland) and purified as described (Skehel, J. et al., (1971). Virology 44:396). The hemagglutinin/phospholipid ratio was determined according to Böttcher (Böttcher et al. (1961). Anal. Chim. Acta 24, 203), and HA-quantification after SOS-PAGE was conducted using the Coomassie extraction method as described by Ball (Ball (1986). Anal. Biochem. 155, 23).
9.2 Preparation of Virosomes
For the preparation of the virosome (IRIV) delivery system, a solution of purified Influenza A/Singapore hemagglutinin (4 mg) in phosphate buffered saline (PBS) was centrifuged for 30 min at 100,000 g and the pellet was dissolved in PBS (1.33 ml) containing 100 mM octaethyfenegtycolmono-decylether (PBS-OEG). Phosphatidylcholine (32 mg; Lipoid, Ludwigshafen, Germany) and phosphatidylethanolamine (6 mg) were dissolved in a total volume of 2.66 ml of PBS-OEG. The phospholipids and the hemagglutinin solutions were mixed and sonicated for 1 min. This solution was centrifuged for 1 hour at 100,000 g and the supernatant was sterile-filtered. Virosomes were then formed by detergent removal using two times 1.5 g of wet SM2 Bio-Beads (BioRad, Glattbrugg, Switzerland) for 1 h each at room temperature with shaking. The virosome solution was stored at 4° C.

9.3 Preparation of Fusion Peptide Coupled to Virosomes (Fusion Peptide-IRIVs)

Fusion peptide-IRIVs were prepared by the detergent removal method. For a final volume of 4 ml, 32 mg egg PC and 4 mg PE were dissolved in 2 ml of PBS, 100 mM OEG (PBS/OEG) and the prepared protein-PE conjugate (1 ml) was added to this mixture. 2 mg HA of inactivated influenza A/Singapore/6/86 virus was centrifuged at 100,000 g for 1 h at 4° C. and the pellet was dissolved in 1 ml of PBS/OEG. The detergent-solubilized phospholipids and viruses were mixed and sonicated for 1 min. This mixture was centrifuged at 100,000 g for 1 h at 18° C. and the supernatant was collected for further steps. Virosomes were then formed by detergent removal using two times 1.5 g of wet SM2 Bio-Beads for 1 h each at room temperature with shaking. The virosome solution was stored at 4° C.

Example 10

Vaccine Composition Containing Fusion Peptide in Combination with Lyophilized Virosomes as a Delivery System 10.1 Preparation of Virosomes Containing TC-Chol Virosomes containing TC-Chol were prepared by the detergent removal method, For a final volume of 4 ml, 32 mg egg PC, 8 mg OPPE and 5 mg cholesterol N-(trimethylammonioethyl)carbamate chloride (TC-chol) were dissolved in 2.6 ml of PBS, 100 mM OEG (PBS/OEG). 2 mg HA of Inactivated A/Singapore/6/86 influenza virus or another influenza A strain was centrifuged at 100,000 g for 1 h at 4° C. and the pellet is dissolved in 1 ml of PBS/OEG. The detergent-solubilized phospholipids and viruses were mixed with 0.4 mL of 50% (w/v) sucrose and sonicated for 1 min. This mixture was centrifuged at 100,000 g for 1 h at 18° C. Virosomes were formed by detergent removal using two times 1.5 g of wet SM2 Bio-Beads for 1 h each at room temperature with shaking. The freshly formed virosomes were then sterile-filtered (0.22 μm) and aliquoted in sterile glass vials. The closed vials are frozen at −70° C. and then lyophilized at −40° C. for 20 h and 10° C. for 2 h. The closed vials were stored frozen until use.

10.2 Preparation of Fusion Peptide Coupled to Lyophilizable Virosomes (Peptide-TIRIVs)

To obtain a TIRIV delivery system with fusion peptide coupled (i.e. covatently associated) to a phospholipid anchor, the protein is coupled to PE as described above and dissolved in the solution containing egg PC, PE and TC-Chol in PBS/OEG, before combining with the detergent solubilized viral HA of inactivated H1N1 influenza virus. The detergent-solubilized phospholipids and viruses are mixed with sucrose to a final concentration of 5% (w/v) and sonicated for 1 min. This mixture is centrifuged at 100,000×g for 1 h at 18° C. Virosomes with the fusion peptide coupled to their membrane are then formed by detergent removal using two times 1.5 g of wet Bio-Beads SM2 for 1 h each at room temperature with shaking. The virosomes are sterile-filtered (0.22 μm) and aliquoted in sterile glass vials. The closed vials are frozen at −70° C. and then lyophilized at −40° C. for 20 h and 10° C. for 2 h. The closed vials are stored frozen until further use.

Reconstitution of the lyophilized TIRIVs was performed with an equal volume of sterile water. The vial was mixed shortly for about 10 sec on the vortex on intermediate level and stored at 4° C. until use.

Example 11

Vaccine Composition Containing Fusion Peptide in Combination with a Montande™ Delivery System Peptides were dissolved in dimethyisufoxide (DMSO) at 20 mg/ml, further diluted in PBS at 1 mg/ml and emulsified at a 1:1 ratio with Montanide ISA™ 51 (Seppic, France) to obtain a final concentration of 0.5 mg/ml. To prepare the emulsion the mixture was vortexed for 30 seconds at 2000 rpm followed by emulsification by syringe-extrusion. For this purpose the mixture was passed 25 times through an 18-gauge connector between two syringes.

Example 12

Vaccine Composition Containing Fusion Peptide in Combination with an ISCOM Delivery System For a final volume of 0.6 mL of vaccine formulation 15 μl of the peptide solution (20 mg/mL in DMSO) was mixed with 150 μl AbISCO®-100 (Isconova, Sweden; 0.48 mg/ml; AbISCO® is composed of purified saponin fractions obtained from a crude extract of the plant *Quillaja saponaria* Molina, phosphatidyl choline and cholesterol) and 435 μl PBS to obtain a final peptide concentration of 0.5 mg/ml.

Example 13

Vaccine Composition Containing Fusion Peptide in Combination with a Tetanus Toxoid (TT) Delivery System Sulphosuccinimidyl-4-(N-maleimidomethyl)cyclohexane-1-carboxylate (Sulfo-SMCC; Apollo Scientific Ltd, UK) was dissolved in PBS at 5 mg/ml. Tetanus toxoid (TT; Statens Serum Institute, Denmark) was diluted with PBS at 0.5 mg/mL. 1 ml TT solution was incubated with 175 μl of the Sulfo-SMCC solution for 30 min at room temperature. 0.5 ml of this Sulfo-SMCC/TT solution was mixed with 0.5 mg peptide dissolved in 1 ml PBS and incubated for 2 hours at RT with shaking. For the final formulation PBS was added to a final volume of 2 ml.

Example 14

Determination of "B Cell Epitopes"

Potential B cell epitopes can be predicted by computation analysis of the Her2/neu amino acid sequence using the ABCpred Prediction Server freely available at www.imtech.res.in/raghava/abcpred/, setting the threshold to 0.51 and the window length for prediction to 16. The ABCpred tool is for prediction of B cell epitopes in an antigen sequence using an artificial neural network described by Saha and Raghava, Proteins 65:40-48, 2006.

The invention claimed is:

1. A fusion peptide comprising three non-contiguous B cell epitopes from the extracellular domain (ECO) of Her2/neu, wherein the fusion peptide comprises a sequence selected from the group consisting of SEQ NOs: 4-10.

2. The fusion peptide of claim 1, wherein the amino acid sequence of the fusion peptide consists of a sequence selected from the group consisting of SEQ ID NOs: 4-10.

3. A method of preparing a fusion peptide of claim 1:
I. via a peptide synthetic method comprising the steps of:
   (i) Sequentially forming peptide bonds linking each amino acid to its respectively neighboring amino acid; and
   (ii) Recovering said fusion peptide;
or
II. via a recombinant method comprising the steps of:
   (i) Providing a nucleic acid comprising a nucleic acid sequence encoding a fusion peptide according to claim 1;
   (ii) Transfecting said nucleic acid into a host cell capable of expressing said nucleic acid sequence;
   (iii) Incubating said host cell under conditions suitable for the expression of said nucleic acid sequence; and
   (iv) Recovering said fusion peptide.

4. A delivery system covalently or non-covalently associated with a fusion peptide of claim 1.

5. The delivery system of claim 4, wherein said delivery system is selected from the group consisting of a virosome, a liposome, a virus-like particle (VLP), tetanus toxoid (TT), a keyhole limpet hemocyanin (KLH), an immunostimulating complex (ISCOM), an emulsion, hepatitis B core antigen (HBc), a nano- or microparticle, an aluminium salt, calcium phosphate, stearyl tyrosine and a viral vector; and a combination of two or more thereof.

6. The delivery system of claim 5, wherein said delivery system is a virosome in which said fusion peptide is encapsulated or to which said fusion peptide is covalently bound.

7. The delivery system of claim 6, wherein said fusion peptide is covalently bound to a viral envelope protein or a lipid component of said virosome.

8. The delivery system of claim 7, wherein said lipid component of the virosome is phosphatidylethanolamine.

9. The delivery system of claim 5, wherein said virosome is an IRIV or a TIRIV.

10. A composition comprising a fusion peptide of claim 1, a delivery system covalently or non-covalently associated with a fusion peptide of claim 1, or a combination thereof.

11. The composition of claim 10, additionally comprising an immunopotentiator.

12. The composition of claim 11, wherein the immunopotentiator is selected from the group consisting of a bacterial toxin, a bacterial cell-surface lipopolysaccharide (LPS), lipid A or a synthetic derivative thereof, an oligopeptide, an alternative pathogen-associated molecular pattern (PAMP), a lipopeptide, a lipoprotein, a peptidoglycan, lipoteichoic acid (LTA), a yeast cell wall component, a glycolipid, viral or bacterial DNA, an oligonucleotide, double-stranded RNA, polyinosinic-polycytidylic acid (poly I:C), single-stranded viral RNA, a small molecule immune potentiator (SMIP), a cytokine, a chemokine, a saponin, a polyphosphazene, a cochleate structure, a suppressor of cytokine signalling small interfering RNA (SaCS siRNA), a Pan DR epitope (PADRE); and a combination of two or more thereof.

13. A pharmaceutical composition comprising the composition of claim 10 and a pharmaceutically acceptable carrier.

14. A method of inducing higher antibody levels against a given B cell epitope than induced by a single peptide containing only that B cell epitope alone in a cancer characterized by expression or over-expression of Her2 in a patient in need thereof, the method comprising the step of administering to said patient an effective amount of a fusion peptide of claim 1, a delivery system covalently or non-covalently associated with a fusion peptide of claim 1 or a combination thereof.

15. The method of claim 14, wherein said cancer is breast cancer.

* * * * *

SEQUENCE LISTING

```
<160> NUMBER OF SEQ ID NOS: 57

<210> SEQ ID NO 1
<211> LENGTH: 23
```

```
<212> TYPE: PRT
<213> ORGANISM: Artificial Sequence
<220> FEATURE:
<221> NAME/KEY: MISC_FEATURE
<223> OTHER INFORMATION: Peptide Fragment PEV601

<400> SEQUENCE: 1

Pro Glu Ser Phe Asp Gly Asp Pro Ala Ser Asn Thr Ala Pro Leu Gln
1               5                   10                  15

Pro Gly Gly Gly Gly Gly Cys
            20

<210> SEQ ID NO 2
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment PEV602

<400> SEQUENCE: 2

Arg Val Leu Gln Gly Leu Pro Arg Glu Tyr Val Asn Ala Arg His Cys
1               5                   10                  15

<210> SEQ ID NO 3
<211> LENGTH: 14
<212> TYPE: PRT
<213> ORGANISM: Artificial Sequence
<220> FEATURE:
<221> NAME/KEY: MISC_FEATURE
<223> OTHER INFORMATION: Peptide Fragment PEV603

<400> SEQUENCE: 3

Tyr Met Pro Ile Trp Lys Phe Pro Asp Glu Glu Gly Ala Cys
1               5                   10

<210> SEQ ID NO 4
<211> LENGTH: 49
<212> TYPE: PRT
<213> ORGANISM: Artificial Sequence
<220> FEATURE:
<221> NAME/KEY: MISC_FEATURE
<223> OTHER INFORMATION: Peptide Fragment PEV604

<400> SEQUENCE: 4

Pro Glu Ser Phe Asp Gly Asp Pro Ala Ser Asn Thr Ala Pro Leu Gln
1               5                   10                  15

Pro Arg Val Leu Gln Gly Leu Pro Arg Glu Tyr Val Asn Ala Arg His
            20                  25                  30

Ser Leu Pro Tyr Met Pro Ile Trp Lys Phe Pro Asp Glu Glu Gly Ala
        35                  40                  45

Cys

<210> SEQ ID NO 5
<211> LENGTH: 47
<212> TYPE: PRT
<213> ORGANISM: Artificial Sequence
<220> FEATURE:
<221> NAME/KEY: MISC_FEATURE
<223> OTHER INFORMATION: Peptide Fragment PEV605

<400> SEQUENCE: 5

Pro Glu Ser Phe Asp Gly Asp Pro Ala Ser Asn Thr Ala Pro Leu Gln
1               5                   10                  15

Pro Arg Val Leu Gln Gly Leu Pro Arg Glu Tyr Val Asn Ala Arg His
```

```
                 20                  25                  30

Ser Tyr Met Pro Ile Trp Lys Phe Pro Asp Glu Glu Gly Ala Cys
        35                  40                  45

<210> SEQ ID NO 6
<211> LENGTH: 47
<212> TYPE: PRT
<213> ORGANISM: Artificial Sequence
<220> FEATURE:
<221> NAME/KEY: MISC_FEATURE
<223> OTHER INFORMATION: Peptide Fragment PEV606

<400> SEQUENCE: 6

Pro Glu Ser Phe Asp Gly Asp Pro Ala Ser Asn Thr Ala Pro Leu Gln
1               5                   10                  15

Pro Tyr Met Pro Ile Trp Lys Phe Pro Asp Glu Glu Gly Ala Ser Arg
            20                  25                  30

Val Leu Gln Gly Leu Pro Arg Glu Tyr Val Asn Ala Arg His Cys
        35                  40                  45

<210> SEQ ID NO 7
<211> LENGTH: 47
<212> TYPE: PRT
<213> ORGANISM: Artificial Sequence
<220> FEATURE:
<221> NAME/KEY: MISC_FEATURE
<223> OTHER INFORMATION: Peptide Fragment PEV607

<400> SEQUENCE: 7

Arg Val Leu Gln Gly Leu Pro Arg Glu Tyr Val Asn Ala Arg His Ser
1               5                   10                  15

Pro Glu Ser Phe Asp Gly Asp Pro Ala Ser Asn Thr Ala Pro Leu Gln
            20                  25                  30

Pro Tyr Met Pro Ile Trp Lys Phe Pro Asp Glu Glu Gly Ala Cys
        35                  40                  45

<210> SEQ ID NO 8
<211> LENGTH: 48
<212> TYPE: PRT
<213> ORGANISM: Artificial Sequence
<220> FEATURE:
<221> NAME/KEY: MISC_FEATURE
<223> OTHER INFORMATION: Peptide Fragment PEV608

<400> SEQUENCE: 8

Arg Val Leu Gln Gly Leu Pro Arg Glu Tyr Val Asn Ala Arg His Ser
1               5                   10                  15

Tyr Met Pro Ile Trp Lys Phe Pro Asp Glu Glu Gly Ala Ser Pro Glu
            20                  25                  30

Ser Phe Asp Gly Asp Pro Ala Ser Asn Thr Ala Pro Leu Gln Pro Cys
        35                  40                  45

<210> SEQ ID NO 9
<211> LENGTH: 47
<212> TYPE: PRT
<213> ORGANISM: Artificial Sequence
<220> FEATURE:
<221> NAME/KEY: MISC_FEATURE
<223> OTHER INFORMATION: Peptide Fragment PEV609

<400> SEQUENCE: 9

Tyr Met Pro Ile Trp Lys Phe Pro Asp Glu Glu Gly Ala Ser Pro Glu
1               5                   10                  15
```

```
Ser Phe Asp Gly Asp Pro Ala Ser Asn Thr Ala Pro Leu Gln Pro Arg
            20                  25                  30

Val Leu Gln Gly Leu Pro Arg Glu Tyr Val Asn Ala Arg His Cys
        35                  40                  45

<210> SEQ ID NO 10
<211> LENGTH: 48
<212> TYPE: PRT
<213> ORGANISM: Artificial Sequence
<220> FEATURE:
<221> NAME/KEY: MISC_FEATURE
<223> OTHER INFORMATION: Peptide Fragment PEV610

<400> SEQUENCE: 10

Tyr Met Pro Ile Trp Lys Phe Pro Asp Glu Glu Gly Ala Ser Arg Val
1               5                   10                  15

Leu Gln Gly Leu Pro Arg Glu Tyr Val Asn Ala Arg His Ser Pro Glu
            20                  25                  30

Ser Phe Asp Gly Asp Pro Ala Ser Asn Thr Ala Pro Leu Gln Pro Cys
            35                  40                  45

<210> SEQ ID NO 11
<211> LENGTH: 1255
<212> TYPE: PRT
<213> ORGANISM: Homo sapiens
<220> FEATURE:
<221> NAME/KEY: MISC_FEATURE
<223> OTHER INFORMATION: Extracellular domain of human Her2/neu

<400> SEQUENCE: 11

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220
```

```
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
    275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
    355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
```

-continued

```
              645                 650                 655
Ala Val Val Gly Ile Leu Leu Val Val Leu Gly Val Val Phe Gly
              660                 665                 670

Ile Leu Ile Lys Arg Arg Gln Gln Lys Ile Arg Lys Tyr Thr Met Arg
              675                 680                 685

Arg Leu Leu Gln Glu Thr Glu Leu Val Glu Pro Leu Thr Pro Ser Gly
690               695                 700

Ala Met Pro Asn Gln Ala Gln Met Arg Ile Leu Lys Glu Thr Glu Leu
705                   710                 715                 720

Arg Lys Val Lys Val Leu Gly Ser Gly Ala Phe Gly Thr Val Tyr Lys
              725                 730                 735

Gly Ile Trp Ile Pro Asp Gly Glu Asn Val Lys Ile Pro Val Ala Ile
              740                 745                 750

Lys Val Leu Arg Glu Asn Thr Ser Pro Lys Ala Asn Lys Glu Ile Leu
              755                 760                 765

Asp Glu Ala Tyr Val Met Ala Gly Val Gly Ser Pro Tyr Val Ser Arg
770               775                 780

Leu Leu Gly Ile Cys Leu Thr Ser Thr Val Gln Leu Val Thr Gln Leu
785               790                 795                 800

Met Pro Tyr Gly Cys Leu Leu Asp His Val Arg Glu Asn Arg Gly Arg
              805                 810                 815

Leu Gly Ser Gln Asp Leu Leu Asn Trp Cys Met Gln Ile Ala Lys Gly
              820                 825                 830

Met Ser Tyr Leu Glu Asp Val Arg Leu Val His Arg Asp Leu Ala Ala
              835                 840                 845

Arg Asn Val Leu Val Lys Ser Pro Asn His Val Lys Ile Thr Asp Phe
850               855                 860

Gly Leu Ala Arg Leu Leu Asp Ile Asp Glu Thr Glu Tyr His Ala Asp
865               870                 875                 880

Gly Gly Lys Val Pro Ile Lys Trp Met Ala Leu Glu Ser Ile Leu Arg
              885                 890                 895

Arg Arg Phe Thr His Gln Ser Asp Val Trp Ser Tyr Gly Val Thr Val
              900                 905                 910

Trp Glu Leu Met Thr Phe Gly Ala Lys Pro Tyr Asp Gly Ile Pro Ala
              915                 920                 925

Arg Glu Ile Pro Asp Leu Leu Glu Lys Gly Glu Arg Leu Pro Gln Pro
              930                 935                 940

Pro Ile Cys Thr Ile Asp Val Tyr Met Ile Met Val Lys Cys Trp Met
945               950                 955                 960

Ile Asp Ser Glu Cys Arg Pro Arg Phe Arg Glu Leu Val Ser Glu Phe
              965                 970                 975

Ser Arg Met Ala Arg Asp Pro Gln Arg Phe Val Val Ile Gln Asn Glu
              980                 985                 990

Asp Leu Gly Pro Ala Ser Pro Leu Asp Ser Thr Phe Tyr Arg Ser Leu
              995                 1000                1005

Leu Glu Asp Asp Asp Met Gly Asp Leu Val Asp Ala Glu Glu Tyr
    1010            1015                1020

Leu Val Pro Gln Gln Gly Phe Phe Cys Pro Asp Pro Ala Pro Gly
    1025            1030                1035

Ala Gly Gly Met Val His His Arg His Arg Ser Ser Ser Thr Arg
    1040            1045                1050

Ser Gly Gly Gly Asp Leu Thr Leu Gly Leu Glu Pro Ser Glu Glu
    1055            1060                1065
```

```
Glu Ala Pro Arg Ser Pro Leu Ala Pro Ser Glu Gly Ala Gly Ser
        1070            1075                1080

Asp Val Phe Asp Gly Asp Leu Gly Met Gly Ala Ala Lys Gly Leu
        1085            1090                1095

Gln Ser Leu Pro Thr His Asp Pro Ser Pro Leu Gln Arg Tyr Ser
        1100            1105                1110

Glu Asp Pro Thr Val Pro Leu Pro Ser Glu Thr Asp Gly Tyr Val
        1115            1120                1125

Ala Pro Leu Thr Cys Ser Pro Gln Pro Glu Tyr Val Asn Gln Pro
        1130            1135                1140

Asp Val Arg Pro Gln Pro Pro Ser Pro Arg Glu Gly Pro Leu Pro
        1145            1150                1155

Ala Ala Arg Pro Ala Gly Ala Thr Leu Glu Arg Pro Lys Thr Leu
        1160            1165                1170

Ser Pro Gly Lys Asn Gly Val Val Lys Asp Val Phe Ala Phe Gly
        1175            1180                1185

Gly Ala Val Glu Asn Pro Glu Tyr Leu Thr Pro Gln Gly Gly Ala
        1190            1195                1200

Ala Pro Gln Pro His Pro Pro Pro Ala Phe Ser Pro Ala Phe Asp
        1205            1210                1215

Asn Leu Tyr Tyr Trp Asp Gln Asp Pro Pro Glu Arg Gly Ala Pro
        1220            1225                1230

Pro Ser Thr Phe Lys Gly Thr Pro Thr Ala Glu Asn Pro Glu Tyr
        1235            1240                1245

Leu Gly Leu Asp Val Pro Val
        1250            1255

<210> SEQ ID NO 12
<211> LENGTH: 17
<212> TYPE: PRT
<213> ORGANISM: Artificial Sequence
<220> FEATURE:
<221> NAME/KEY: MISC_FEATURE
<223> OTHER INFORMATION: Peptide Fragment PEV11

<400> SEQUENCE: 12

Pro Glu Ser Phe Asp Gly Asp Pro Ala Ser Asn Thr Ala Pro Leu Gln
1               5                   10                  15

Pro

<210> SEQ ID NO 13
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 13

Cys Ala His Tyr Lys Asp Pro Pro Phe Cys Val Ala Arg Cys Pro Ser
1               5                   10                  15

<210> SEQ ID NO 14
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment
```

```
<400> SEQUENCE: 14

Tyr Gly Leu Gly Met Glu His Leu Arg Glu Val Arg Ala Val Thr Ser
1               5                   10                  15

<210> SEQ ID NO 15
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 15

Leu Gly Ser Gly Leu Ala Leu Ile His His Asn Thr His Leu Cys Phe
1               5                   10                  15

<210> SEQ ID NO 16
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 16

Glu Val Thr Ala Glu Asp Gly Thr Gln Arg Cys Glu Lys Cys Ser Lys
1               5                   10                  15

<210> SEQ ID NO 17
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 17

Gly Ala Ser Cys Val Thr Ala Cys Pro Tyr Asn Tyr Leu Ser Thr Asp
1               5                   10                  15

<210> SEQ ID NO 18
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 18

Ala Ala Gly Cys Thr Gly Pro Lys His Ser Asp Cys Leu Ala Cys Leu
1               5                   10                  15

<210> SEQ ID NO 19
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 19

Leu Glu Glu Ile Thr Gly Tyr Leu Tyr Ile Ser Ala Trp Pro Asp Ser
1               5                   10                  15

<210> SEQ ID NO 20
<211> LENGTH: 16
<212> TYPE: PRT
```

```
<213> ORGANISM: Artificial Sequence
<220> FEATURE:
<221> NAME/KEY: MISC_FEATURE
<223> OTHER INFORMATION: Peptide Fragment

<400> SEQUENCE: 20

Thr Gln Arg Cys Glu Lys Cys Ser Lys Pro Cys Ala Arg Val Cys Tyr
1               5                   10                  15

<210> SEQ ID NO 21
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 21

Gly His Cys Trp Gly Pro Gly Pro Thr Gln Cys Val Asn Cys Ser Gln
1               5                   10                  15

<210> SEQ ID NO 22
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 22

Met Pro Ile Trp Lys Phe Pro Asp Glu Glu Gly Ala Cys Gln Pro Cys
1               5                   10                  15

<210> SEQ ID NO 23
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 23

Pro Ala Ser Asn Thr Ala Pro Leu Gln Pro Glu Gln Leu Gln Val Phe
1               5                   10                  15

<210> SEQ ID NO 24
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 24

Pro Glu Gly Arg Tyr Thr Phe Gly Ala Ser Cys Val Thr Ala Cys Pro
1               5                   10                  15

<210> SEQ ID NO 25
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 25

Ala Ser Thr Gln Val Cys Thr Gly Thr Asp Met Lys Leu Arg Leu Pro
1               5                   10                  15
```

<210> SEQ ID NO 26
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 26

Ala Cys His Pro Cys Ser Pro Met Cys Lys Gly Ser Arg Cys Trp Gly
1               5                   10                  15

<210> SEQ ID NO 27
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 27

Gln Asp Thr Ile Leu Trp Lys Asp Ile Phe His Lys Asn Asn Gln Leu
1               5                   10                  15

<210> SEQ ID NO 28
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 28

Gly Pro Glu Ala Asp Gln Cys Val Ala Cys Ala His Tyr Lys Asp Pro
1               5                   10                  15

<210> SEQ ID NO 29
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 29

Ser Arg Cys Trp Gly Glu Ser Ser Glu Asp Cys Gln Ser Leu Thr Arg
1               5                   10                  15

<210> SEQ ID NO 30
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 30

Pro Ala Ser Pro Glu Thr His Leu Asp Met Leu Arg His Leu Tyr Gln
1               5                   10                  15

<210> SEQ ID NO 31
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 31

Tyr Val Asn Ala Arg His Cys Leu Pro Cys His Pro Glu Cys Gln Pro
1               5                   10                  15

<210> SEQ ID NO 32
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 32

His Ser Asp Cys Leu Ala Cys Leu His Phe Asn His Ser Gly Ile Cys
1               5                   10                  15

<210> SEQ ID NO 33
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 33

Ala Leu Thr Leu Ile Asp Thr Asn Arg Ser Arg Ala Cys His Pro Cys
1               5                   10                  15

<210> SEQ ID NO 34
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 34

Ala Leu Ala Val Leu Asp Asn Gly Asp Pro Leu Asn Asn Thr Thr Pro
1               5                   10                  15

<210> SEQ ID NO 35
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 35

Ala Leu Val Thr Tyr Asn Thr Asp Thr Phe Glu Ser Met Pro Asn Pro
1               5                   10                  15

<210> SEQ ID NO 36
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 36

Arg Cys Lys Gly Pro Leu Pro Thr Asp Cys Cys His Glu Gln Cys Ala
1               5                   10                  15

<210> SEQ ID NO 37
<211> LENGTH: 16

```
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 37

Gln Pro Cys Pro Ile Asn Cys Thr His Ser Cys Val Asp Leu Asp Asp
1               5                   10                  15

<210> SEQ ID NO 38
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 38

Val Ala Arg Cys Pro Ser Gly Val Lys Pro Asp Leu Ser Tyr Met Pro
1               5                   10                  15

<210> SEQ ID NO 39
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 39

Val His Thr Val Pro Trp Asp Gln Leu Phe Arg Asn Pro His Gln Ala
1               5                   10                  15

<210> SEQ ID NO 40
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 40

Tyr Ile Ser Ala Trp Pro Asp Ser Leu Pro Asp Leu Ser Val Phe Gln
1               5                   10                  15

<210> SEQ ID NO 41
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 41

Cys Lys Lys Ile Phe Gly Ser Leu Ala Phe Leu Pro Glu Ser Phe Asp
1               5                   10                  15

<210> SEQ ID NO 42
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 42

Asn Gly Asp Pro Leu Asn Asn Thr Thr Pro Val Thr Gly Ala Ser Pro
```

<210> SEQ ID NO 43
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 43

Leu Gln Asp Ile Gln Glu Val Gln Gly Tyr Val Leu Ile Ala His Asn
 1               5                  10                  15

<210> SEQ ID NO 44
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 44

Val Cys Ala Gly Gly Cys Ala Arg Cys Lys Gly Pro Leu Pro Thr Asp
 1               5                  10                  15

<210> SEQ ID NO 45
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 45

His Pro Glu Cys Gln Pro Gln Asn Gly Ser Val Thr Cys Phe Gly Pro
 1               5                  10                  15

<210> SEQ ID NO 46
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 46

Gly Val Leu Ile Gln Arg Asn Pro Gln Leu Cys Tyr Gln Asp Thr Ile
 1               5                  10                  15

<210> SEQ ID NO 47
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 47

Leu Gln Val Ile Arg Gly Arg Ile Leu His Asn Gly Ala Tyr Ser Leu
 1               5                  10                  15

<210> SEQ ID NO 48
<211> LENGTH: 16
<212> TYPE: PRT
<213> ORGANISM: Artificial Sequence
<220> FEATURE:
<221> NAME/KEY: MISC_FEATURE

```
<223> OTHER INFORMATION: Peptide Fragment

<400> SEQUENCE: 48

Glu Ser Phe Asp Gly Asp Pro Ala Ser Asn Thr Ala Pro Leu Gln Pro
1               5                   10                  15

<210> SEQ ID NO 49
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 49

Ala Cys Pro Tyr Asn Tyr Leu Ser Thr Asp Val Gly Ser Cys Thr Leu
1               5                   10                  15

<210> SEQ ID NO 50
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 50

Pro Val Thr Gly Ala Ser Pro Gly Gly Leu Arg Glu Leu Gln Leu Arg
1               5                   10                  15

<210> SEQ ID NO 51
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 51

Cys Val Asp Leu Asp Asp Lys Gly Cys Pro Ala Glu Gln Arg Ala Ser
1               5                   10                  15

<210> SEQ ID NO 52
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 52

Asn His Ser Gly Ile Cys Glu Leu His Cys Pro Ala Leu Val Thr Tyr
1               5                   10                  15

<210> SEQ ID NO 53
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 53

Gly Ser Val Thr Cys Phe Gly Pro Glu Ala Asp Gln Cys Val Ala Cys
1               5                   10                  15

<210> SEQ ID NO 54
```

```
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 54

Trp Gly Leu Leu Leu Ala Leu Leu Pro Pro Gly Ala Ala Ser Thr Gln
1               5                   10                  15

<210> SEQ ID NO 55
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 55

Phe Leu Arg Gly Gln Glu Cys Val Glu Glu Cys Arg Val Leu Gln Gly
1               5                   10                  15

<210> SEQ ID NO 56
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 56

Gly Thr Gln Leu Phe Glu Asp Asn Tyr Ala Leu Ala Val Leu Asp Asn
1               5                   10                  15

<210> SEQ ID NO 57
<211> LENGTH: 16
<212> TYPE: PRT
<213> ORGANISM: Artificial Sequence
<220> FEATURE:
<221> NAME/KEY: MISC_FEATURE
<223> OTHER INFORMATION: Peptide Fragment

<400> SEQUENCE: 57

Gly Val Lys Pro Asp Leu Ser Tyr Met Pro Ile Trp Lys Phe Pro Asp
1               5                   10                  15
```